(12) United States Patent
Aksyuk et al.

(10) Patent No.: US 10,161,961 B2
(45) Date of Patent: Dec. 25, 2018

(54) MICROFABRICATED OPTICAL PROBE

(71) Applicant: The United States of America, as represented by the Secretary of Commerce, Washington, DC (US)

(72) Inventors: Vladimir A. Aksyuk, Gaithersburg, MD (US); Kartik Srinivasan, Rockville, MD (US); Thomas Michels, Dortmund (DE)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 15/808,150

(22) Filed: Nov. 9, 2017

(65) Prior Publication Data
US 2018/0210009 A1    Jul. 26, 2018

Related U.S. Application Data

(60) Provisional application No. 62/450,661, filed on Jan. 26, 2017.

(51) Int. Cl.
| | | |
|---|---|---|
| *G01N 21/17* | (2006.01) | |
| *G02B 6/02* | (2006.01) | |
| *H01L 21/67* | (2006.01) | |
| *G01Q 70/08* | (2010.01) | |
| *G01Q 70/02* | (2010.01) | |
| *G03F 7/20* | (2006.01) | |

(52) U.S. Cl.
CPC ............. *G01Q 70/08* (2013.01); *G01N 21/17* (2013.01); *G01Q 70/02* (2013.01); *G02B 6/0208* (2013.01); *G03F 7/2049* (2013.01); *H01L 21/67* (2013.01)

(58) Field of Classification Search
USPC ............ 385/31, 38, 43, 117, 118, 121, 147; 850/6, 29, 32, 45, 56
See application file for complete search history.

(56) References Cited

U.S. PATENT DOCUMENTS 6,785,445 B2 * 8/2004 Kuroda .................. B82Y 20/00
                                                                385/117
8,997,258 B2 * 3/2015 Aksyuk .................. G01Q 20/02
                                                                356/237.2

(Continued)

OTHER PUBLICATIONS

Michels, T, et al., Optical probe for nondestructive wafer-scale characterization of photonic elements, Journal of latex class files, Dec. 27, 2012, vol. 11, No. 4.

(Continued)

*Primary Examiner* — Bernard Souw
(74) *Attorney, Agent, or Firm* — Office of Chief Counsel for National Institute of Standards and Technology

(57) ABSTRACT

A microfabricated optical probe includes: a cantilever; an optical waveguide disposed at a periphery of the cantilever and including an optical loop, the optical loop being disposed coplanar with the cantilever; a mechanical support interposed between and interconnecting the cantilever and the optical waveguide with the mechanical support such that the cantilever and optical waveguide move together; and a substrate on which the cantilever is disposed and from which the cantilever and the optical loop protrude, wherein the cantilever and the optical waveguide flex independently of the substrate.

12 Claims, 26 Drawing Sheets

(56) References Cited

U.S. PATENT DOCUMENTS

2002/0154859 A1* 10/2002 Kuroda .................. B82Y 20/00
   385/31
2014/0338074 A1* 11/2014 Aksyuk .................. G01Q 20/02
   850/6

OTHER PUBLICATIONS

Michels, T. et al., Fabrication Process for an Optomechanical Transducer Platform with Integrated Actuation, Journal of Research of NIST, 2016, vol. 121, https://doi.org/10.6028/jres.121.028.

* cited by examiner

210  Silicon on insulator wafer

212  Define features in Si layer via lithography, etch, on the like

213  Deposit oxide

214  Pattern and etch anchor holes in SiO$_2$

216  Deposit nitride, conformal forms connection to Si through anchor holes

MICROFABRICATED OPTICAL PROBE

CROSS REFERENCE TO RELATED APPLICATIONS

This application claims the benefit of U.S. Provisional Patent Application Ser. No. 62/450,661, filed Jan. 26, 2017, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, Md., 20899; voice (301) 301-975-2573; email tpo@nist.gov; reference NIST Docket Number 17-012US1.

BRIEF DESCRIPTION

Disclosed is a microfabricated optical probe comprising: a cantilever; an optical waveguide disposed at a periphery of the cantilever and comprising an optical loop, the optical loop being disposed coplanar with the cantilever; a mechanical support interposed between and interconnecting the cantilever and the optical waveguide with the mechanical support such that the cantilever and optical waveguide move together; and a substrate on which the cantilever is disposed and from which the cantilever and the optical loop protrude, wherein the cantilever and the optical waveguide flex independently of the substrate.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

Advantageously and unexpectedly, it has been discovered that a microfabricated optical probe described herein can be batch fabricated at wafer scale and part of a scanning probe testing instrument. Indeed, integrated photonics research and manufacturing requires such an optical probe for in-line nondestructive optical testing of devices. The microfabricated optical probe is useful without dedicated or large coupling areas in a photonic circuit and provides control over a degree, location, wavelength or direction of optical coupling. Moreover, the microfabricated optical probe has high sensitivity and resistant to deleterious effects due to mechanical vibration that occur in making precision in-line testing of photonics.

Figure 1:
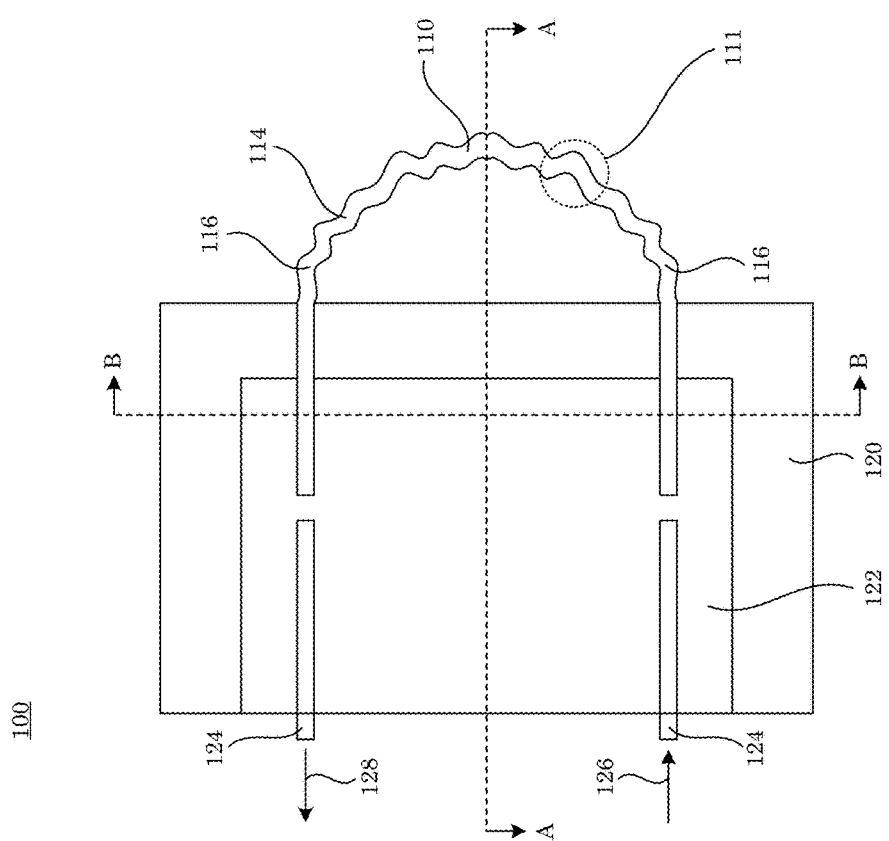
FIG. 1 shows a top view of a microfabricated optical probe.
Figure 2:
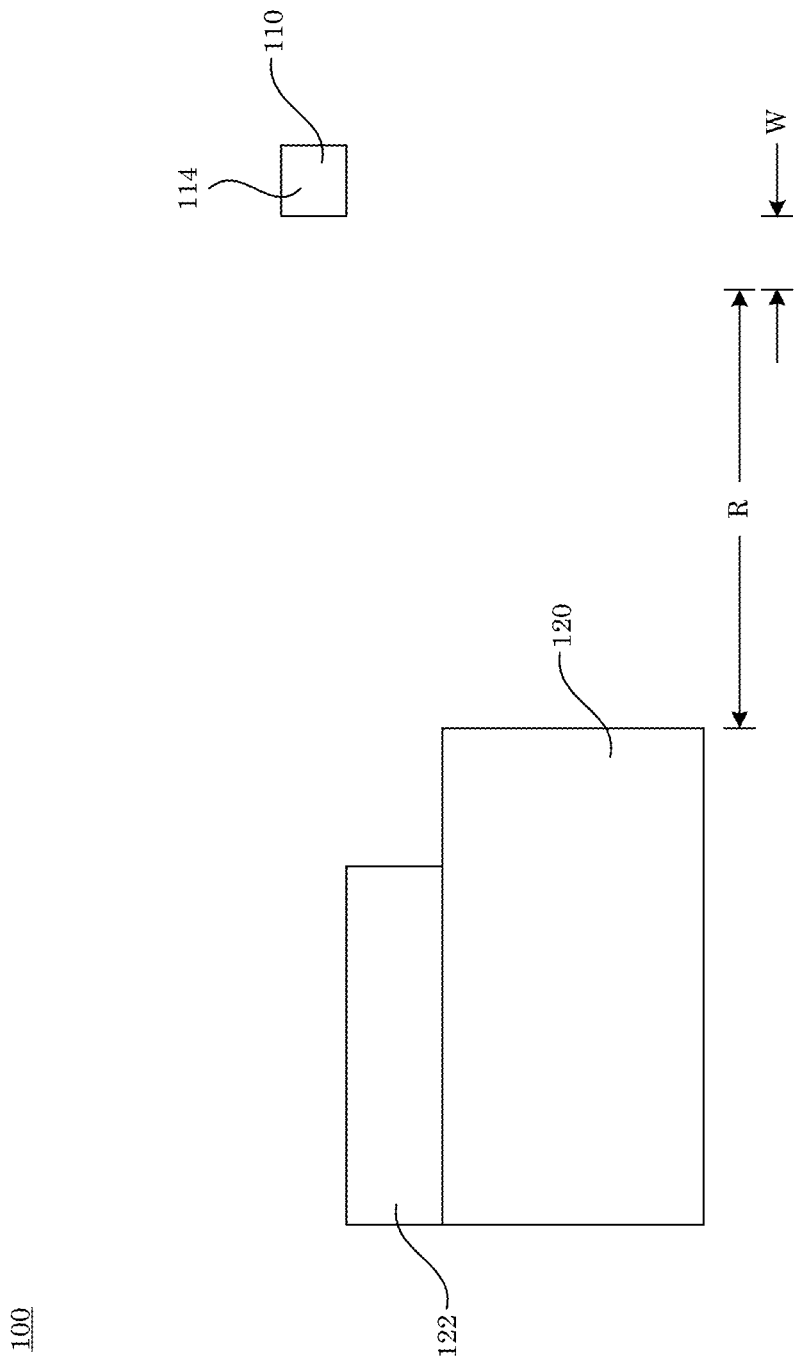
FIG. 2 shows a cross-section along line A-A of the microfabricated optical probe shown in FIG. 1.
Figure 3:
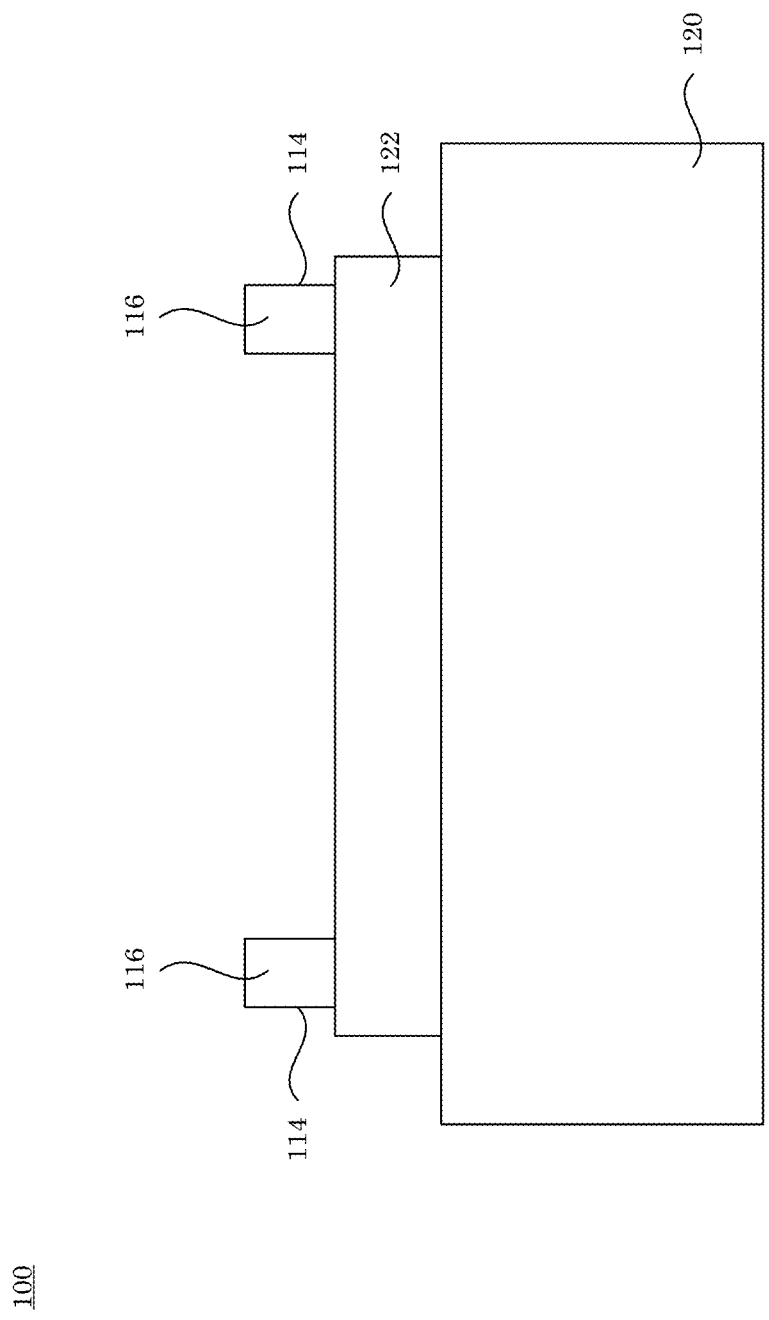
FIG. 3 shows a cross-section along line B-B of the microfabricated optical probe shown in FIG. 1.

In an embodiment, with reference to FIG. 1, FIG. 2, and FIG. 3, microfabricated optical probe 100 includes optical waveguide 114 disposed on substrate 120 and optical loop 110 that disposed on and protruding from substrate 120. Optical loop 110 includes structured region 111. A shape and width of optical loop 110 provides a selected optical property for optical loop 110.

According to an embodiment, microfabricated optical probe 100 includes first single mode optical fiber 124 in optical communication with optical waveguide 114 and that communicates primary light 126 to optical waveguide 114. First arm 116 of optical waveguide 114 is in optical communication with first single mode optical fiber 124 to receive primary light 126 from first single mode optical fiber 124. Moreover, second single mode optical fiber 124 is in optical communication with optical waveguide 114 and receives output light 128 from optical waveguide 114 via second arm 116 that is in optical communication with second single mode optical fiber 124 to communicate output light 128 to second single mode optical fiber 124. Output light 128 may be the same or different from primary light 126 in intensity, phase and spectral content.

During optical probe operation, a portion of the primary light 126 traveling in loop 110 interacts with a device or structure that is located proximal to loop 110 and is being probed, whereby a portion of primary light field enters the device or structure being probed. A portion of primary light 126 may exit the loop and be scattered by the device or structure. A portion of the primary light 126 may enter the device or structure and be absorbed. A portion of the primary light 126 may enter the device or structure and travel to a portion of the device or structure distant from the loop. A portion of the primary light 128 entering a devices or structure may then re-enter the loop. The intensity, optical phase and optical frequency of such re-entering light may be modified by its interaction with the device or structure. Additionally, light otherwise present within the device or structure may enter the loop. Output light 128 may include of a portion of primary light 126 that traveled through the loop without interacting with the device or structure, a portion of primary light 126 that re-entered the loop after interacting with the device or structure, additional light that entered the loop from the device or structure or a coherent or incoherent combination thereof. Primary light 126 may contain one, multiple or continuum of spectral components. Primary light 126 may be used to excite an external device or structure, optically probe it, or both. Output light 128 may contain one, multiple or continuum of spectral components. Output light 128 may include information about characteristics of an external device or structure, about its operation, about light present in a device or structure, or a combination thereof.

Unexpectedly, structured region 111 can be used to control interaction of the primary light 126 with the device or structure and to control collection of the light from the device or structure into the output light 128. The structured region 111 may include gradual tapering or extending of loop width, thereby modifying the wavelengths of light traveling within the loop 110 and modifying decay rates of the evanescent light fields proximal to loop 110. Additionally, structured region 111 may contain multiple periodic or aperiodic changes in the width and shape of the loop 110. Structured region 111 may contain a periodic or aperiodic array of holes, protrusions or other structures. Structured region 111 may form a photonic crystal. Unexpectedly, by choosing the various shapes and materials forming structured region 111, the optical interaction between the loop 110 and external device or structure may be modified as required. Interaction for specific wavelengths of light may be enhanced or suppressed. Primary light 126 may be controlled to couple specifically to waveguides, resonators or other structured within a device, while not being scattered into undesired regions, such as cladding layers, other waveguides or free space. Output light 128 may be controlled to originate from specific waveguides, resonators or other structured within a device, while not being collected from undesired regions, such as cladding layers, other waveguides or free space.

Microfabricated optical probe 100 can include optical cladding layer 122 interposed between waveguide 114 and substrate 120 such that optical loop 110 protrudes from optical cladding layer 122. Optical cladding layer 122 optically decouples optical waveguide 114 from substrate 120 so that primary light 126 and output light 128 can be freely communicated through optical waveguide 114 without loss to substrate 120.

Figure 4:
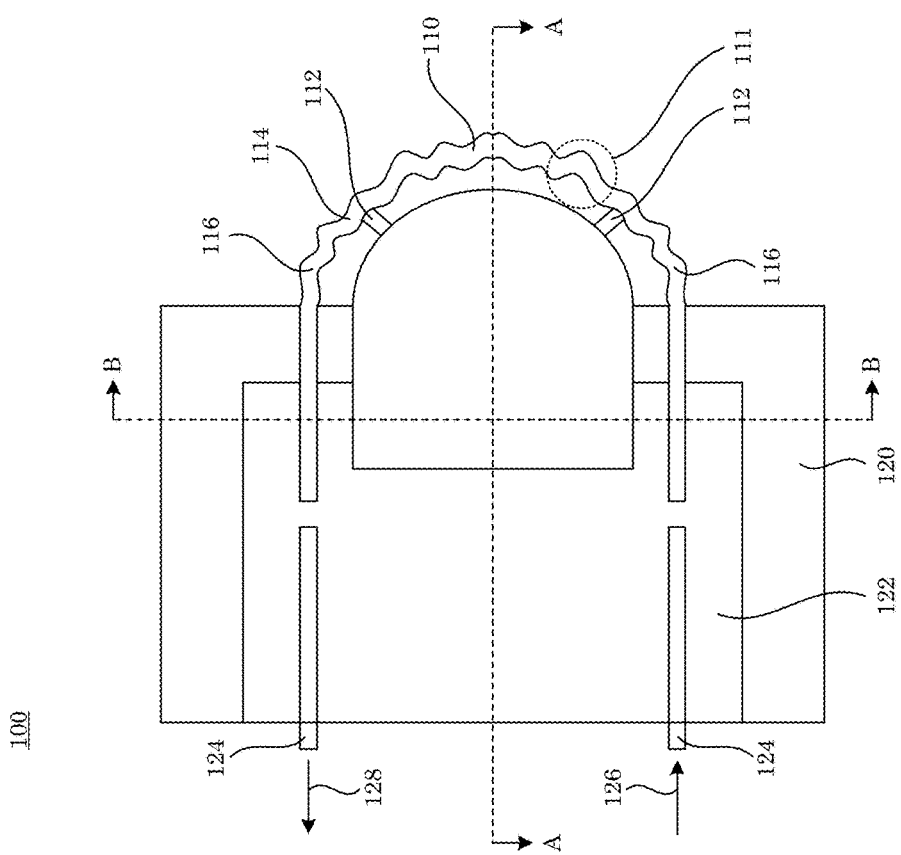
FIG. 4 shows a top view of a microfabricated optical probe.
Figure 5:
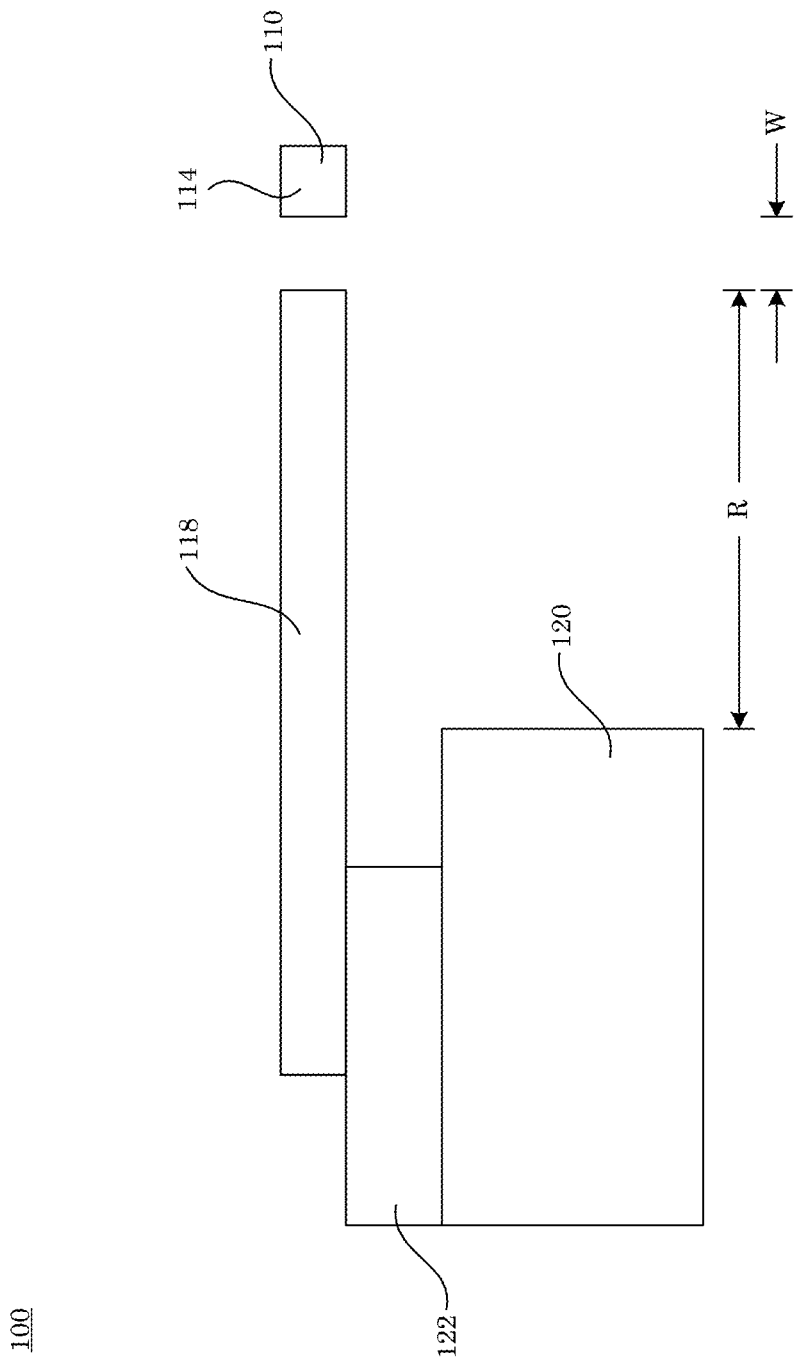
FIG. 5 shows a cross-section along line A-A of the microfabricated optical probe shown in FIG. 4.

In an embodiment, with reference to FIG. 4, FIG. 5, and FIG. 5, microfabricated optical probe 100 includes cantilever 118; optical waveguide 114 disposed at a periphery of cantilever 118 and including optical loop 110 in which optical loop 110 is disposed coplanar with cantilever 118. Microfabricated optical probe 100 also includes mechanical support 112 interposed between and interconnecting cantilever 118 and optical waveguide 114 with mechanical support 112 such that the motions of cantilever 118 and optical waveguide 114 are coupled. In one embodiment, motion of the optical loop 110 results in out-of-plane bending motion of cantilever 118. Mechanical support 112 may allow motion of loop 110 relative to cantilever 118. In an embodiment, optical loop 110 and cantilever 118 move together out-of-plane but optical loop 110 is allowed to move toward or away from cantilever 118 in the plane containing cantilever 118 and optical loop 110. Microfabricated optical probe 100 further includes substrate 120 on which cantilever 118 is disposed and from which cantilever 118 and optical loop 110 protrude. Here, cantilever 118 and optical waveguide 114 flex independently of substrate 120. Optical loop 110 can contain structured region 111 to control and tailor the optical properties of loop 110 and its optical interactions with external device.

According to an embodiment, microfabricated optical probe 100 includes first single mode optical fiber 124 in optical communication with optical waveguide 114 and that communicates primary light 126 to optical waveguide 114. First arm 116 of optical waveguide 114 is in optical communication with first single mode optical fiber 124 to receive primary light 126 from first single mode optical fiber 124. Moreover, second single mode optical fiber 124 is in optical communication with optical waveguide 114 and receives output light 128 from optical waveguide 114 via second arm 116 that is in optical communication with second single mode optical fiber 124 to communicate output light 128 to second single mode optical fiber 124. Output light 128 may include of a portion of primary light 126 that traveled through the loop without interacting with an external device or structure, a portion of primary light 126 that re-entered the loop after interacting with a device or structure, additional light that entered the loop from a device or structure or a coherent or incoherent combination thereof. Primary light 126 may contain one, multiple or continuum of spectral components. Primary light 126 may be used to excite an external device or structure, optically probe it, or both. Output light 128 may contain one, multiple or continuum of spectral components. Output light 128 may convey information about characteristics of an external device or structure, about its operation, about light present in a device or structure, or a combination thereof.

Microfabricated optical probe 100 can include optical cladding layer 122 interposed between cantilever 118, waveguide 114 and substrate 120 such that cantilever 118 and optical loop 110 protrude from optical cladding layer 122. Optical cladding layer 122 optically decouples optical waveguide 114 from substrate 120 so that primary light 126 and output light 128 can be freely communicated through optical waveguide 114 without loss to substrate 120.

Figure 7:
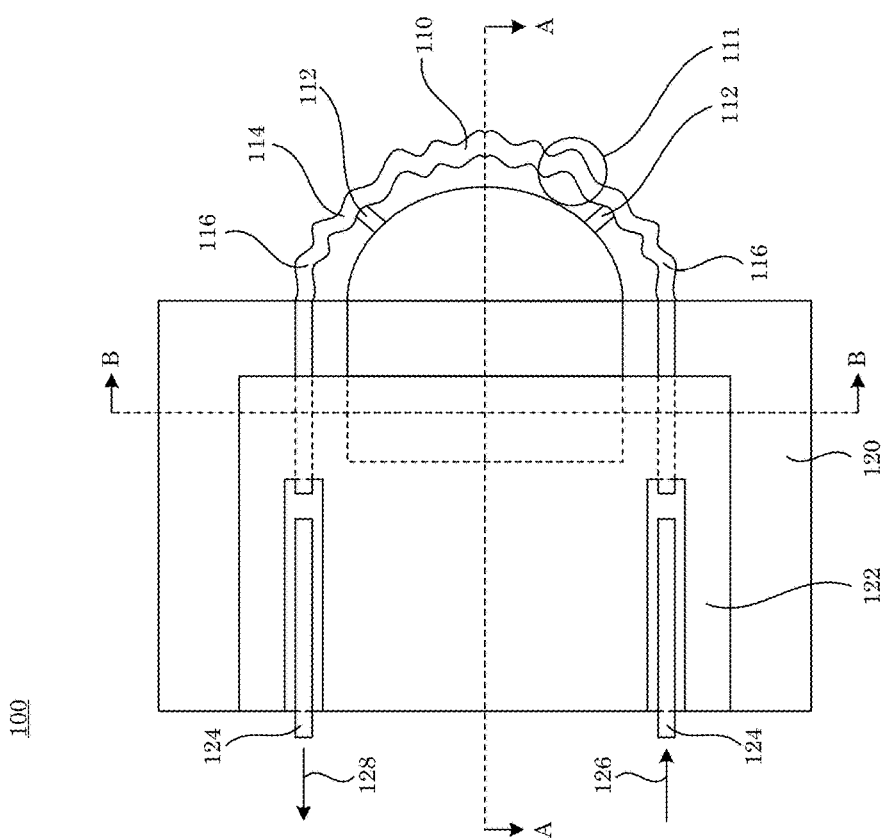
FIG. 7 shows a top view of a microfabricated optical probe.
Figure 8:
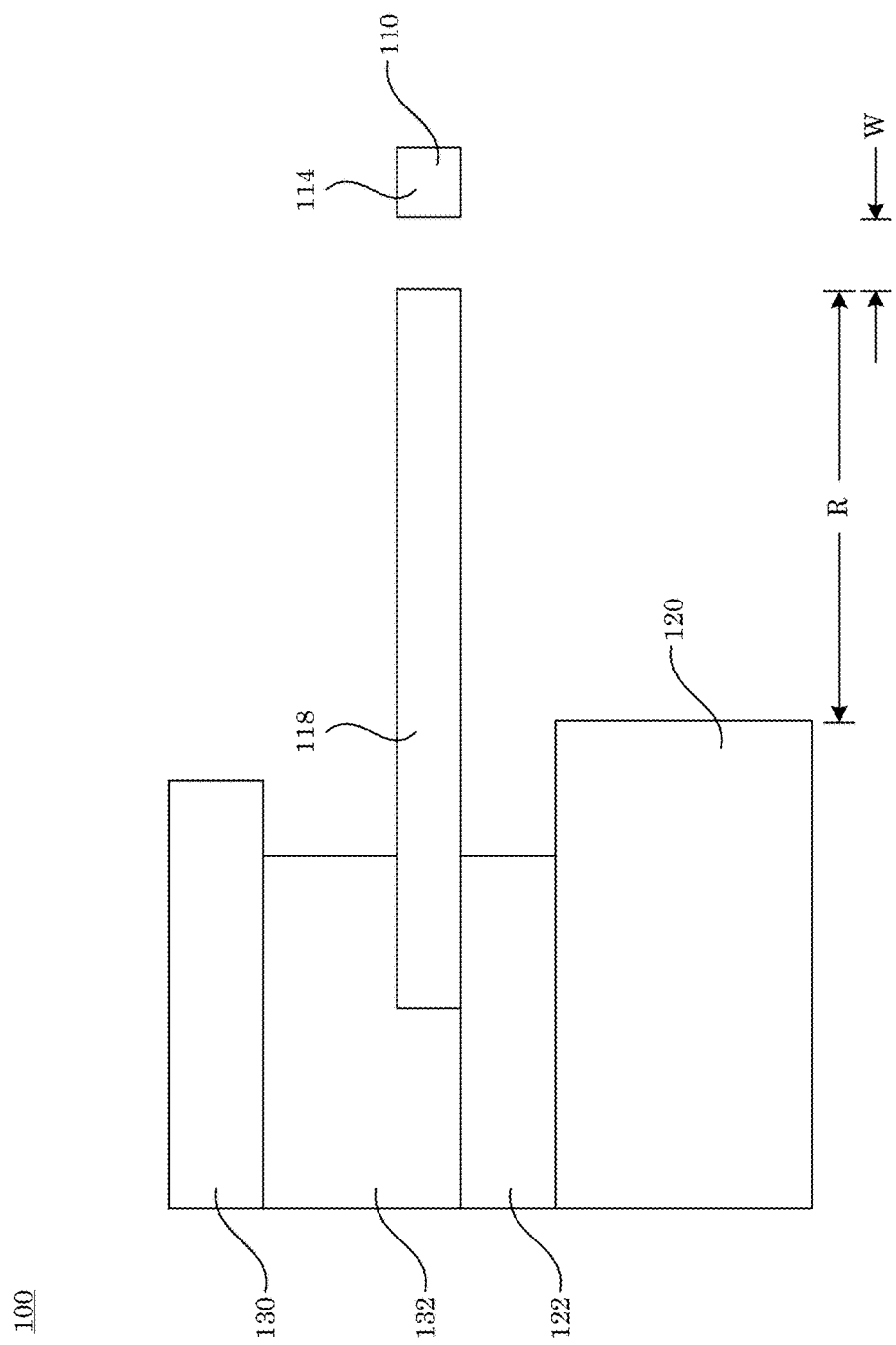
FIG. 8 shows a cross-section along line A-A of the microfabricated optical probe shown in FIG. 7.
Figure 9:
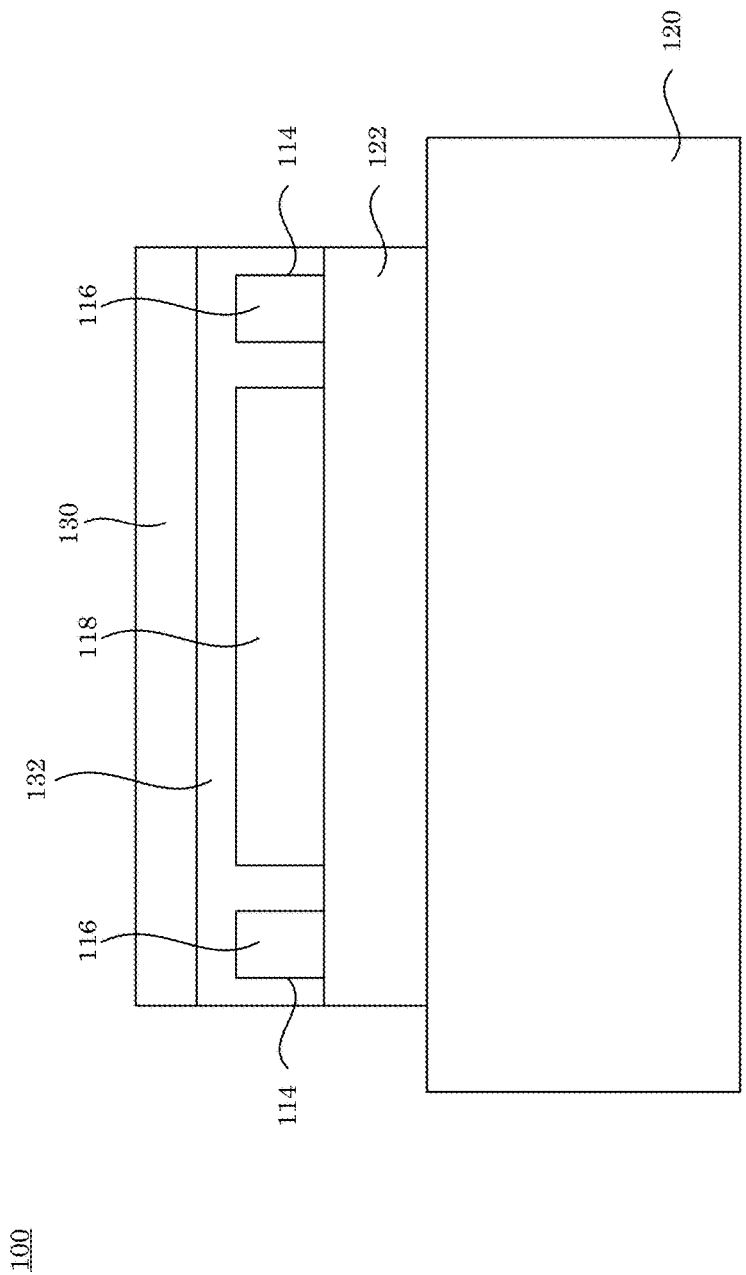
FIG. 9 shows a cross-section along line B-B of the microfabricated optical probe shown in FIG. 7.
Figure 10:
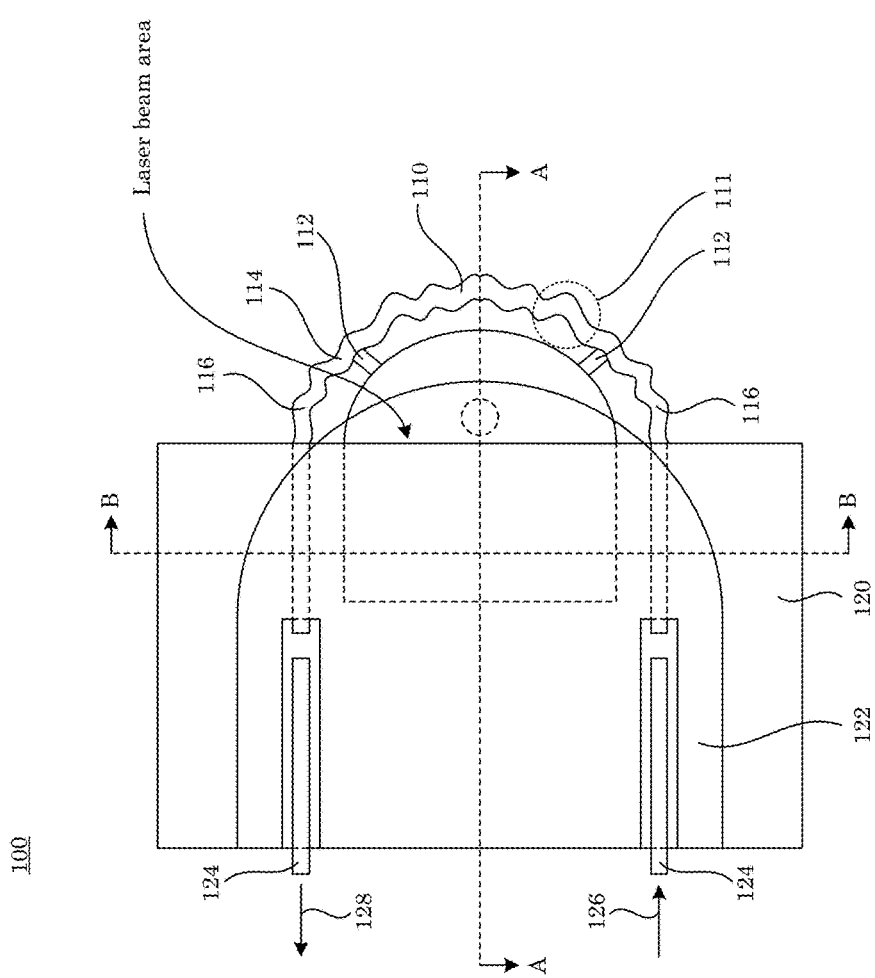
FIG. 10 shows a top view of a microfabricated optical probe.
Figure 11:
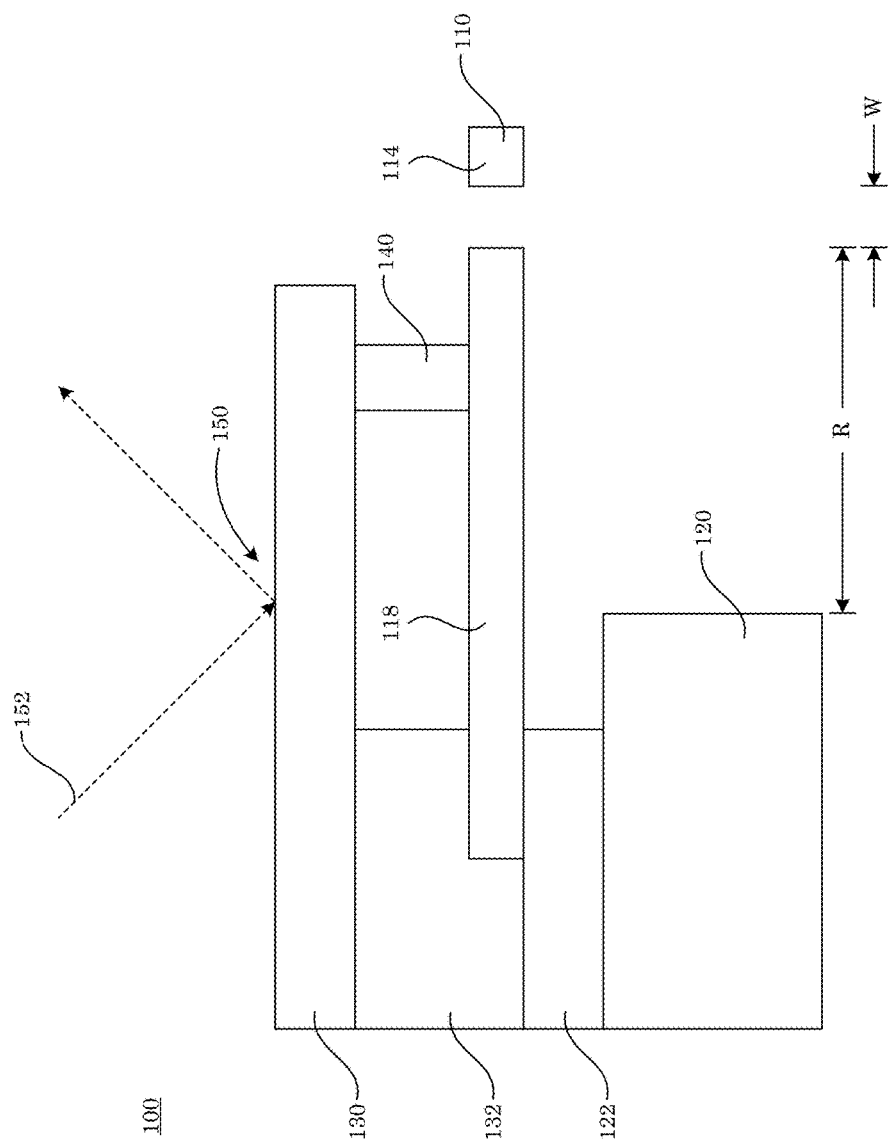
FIG. 11 shows a cross-section along line A-A of the microfabricated optical probe shown in FIG. 10.
Figure 12:
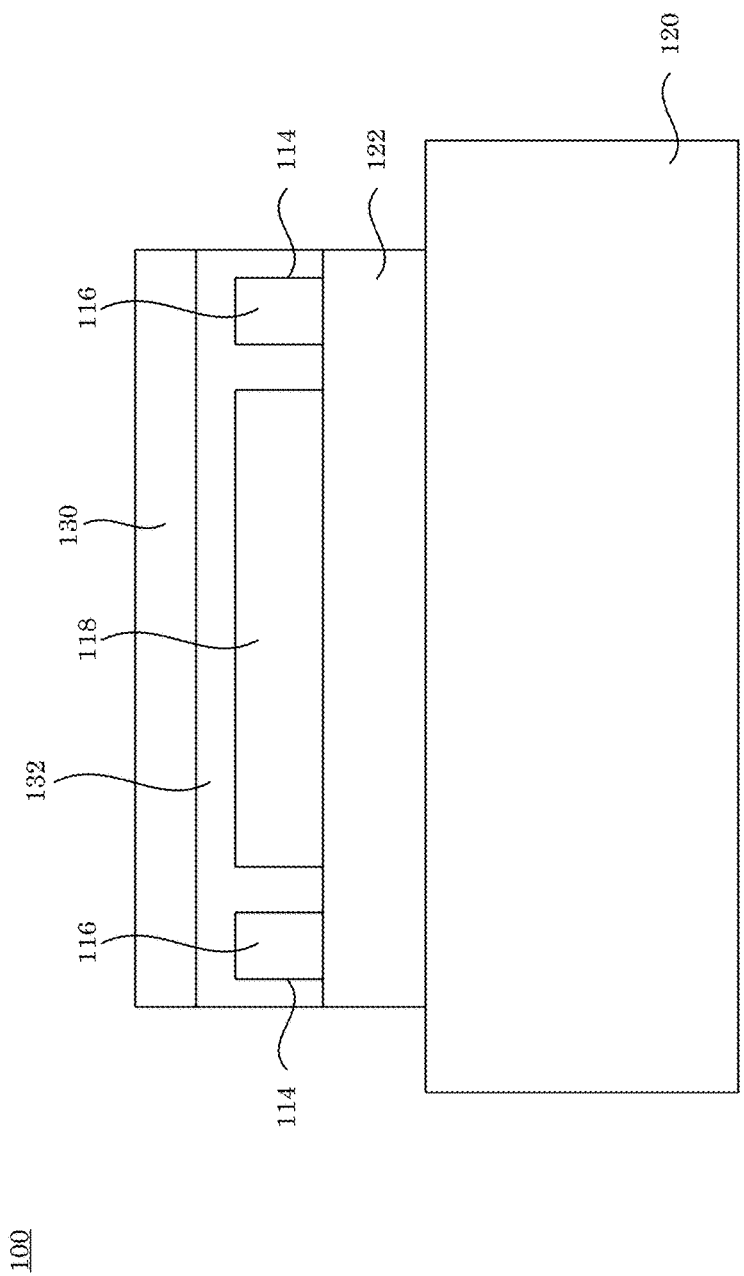
FIG. 12 shows a cross-section along line B-B of the microfabricated optical probe shown in FIG. 10.

In an embodiment, with reference to FIG. 7, FIG. 8, and FIG. 9, microfabricated optical probe 100 can include cover layer 130 disposed on cantilever 118 such that the cantilever is interposed between the substrate and the cover layer. Here, with reference to FIG. 10, FIG. 11, and FIG. 12, cover layer 130 can extend beyond substrate 120 along cantilever 118 and expose optical loop 110 of optical waveguide 114. Pedestal 140 is interposed between cantilever 118 and cover layer 130 so that cover layer 130 is spaced apart from cantilever 118. Second optical cladding layer 132 can be interposed between cantilever 118 and cover layer 130, wherein cantilever 118 and optical loop 110 protrude from second optical cladding layer 132. Second optical cladding layer 132 optically decouples optical waveguide 114 from cover layer 130 so that primary light 126 and output light 128 can be freely communicated through optical waveguide 114 without loss to cover layer 130. Cover layer 130 provides mechanical support to cantilever 118. As shown in FIG. 10 and FIG. 11, cover layer 130 can include laser beam area 150 to reflect laser beam 152. Laser beam 152 can be used to detect motion of cantilever 118 a displacement of cover layer 130. Laser beam area 150 can be selectively reflective for laser beam 152.

It is contemplated that distance R between a proximal edge of substrate 130 and proximate surface of optical loop 110 of optical waveguide 114 is effective to allow flexural motion of optical loop 110. In an embodiment, optical loop 110 has a size given by distance R. In another embodiment the optical loop 110 has a size smaller than distance R. In an embodiment the optical loop 110 is round. Distance R can be from 3 micrometers to 1 mm, specifically from 10 micrometers to 300 micrometers, and more specifically from 20 micrometers to 150 micrometers. The size of optical loop 110 an be from 3 micrometers to 200 micrometers, specifically from 5 micrometers to 50 micrometers, and more specifically from 10 micrometers to 20 micrometers. The width of optical loop 110 an be from 10 nm to 5 micrometers, specifically from 50 nm to 1 micrometer, and more specifically from 100 nm to 500 nm. The width of the structured region 111 can vary in the range from 10 nm to 5 micrometers, specifically from 50 nm to 1 micrometer, and more specifically from 100 nm to 500 nm.

Figure 13:
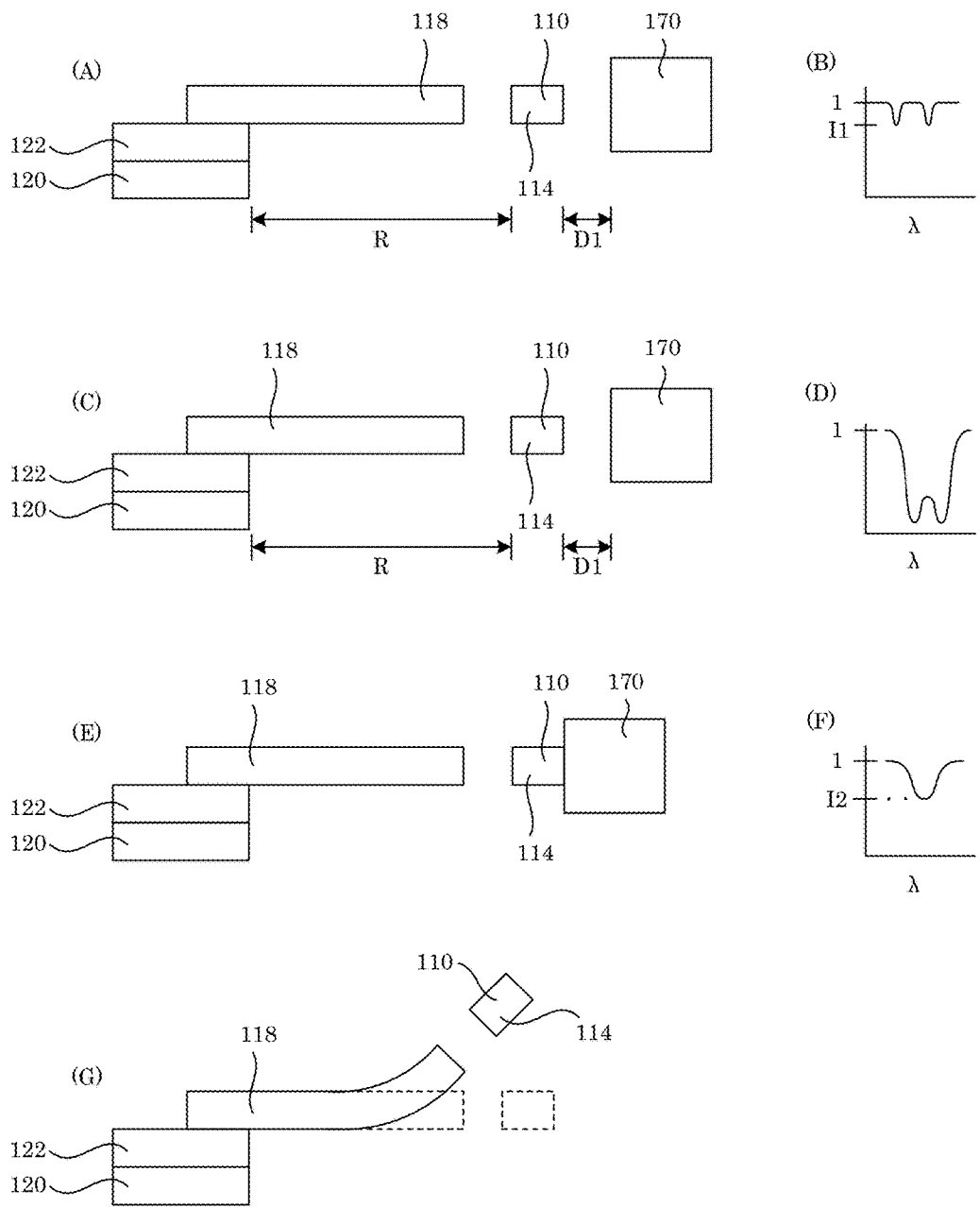
FIG. 13 shows a microfabricated optical probe disposed proximate to a photonic device such that the microfabricated optical probe and photonic device are: optically under coupled in panel A and panel BD, optimally optically coupled panel C and panel D, optically over coupled in panel E and panel F, and flexed with respect to a substrate on which the microfabricated optical probe and optical loop are disposed in panel G.

In an embodiment, with reference to FIG. 13, optical waveguide 114 receives primary light 126 and communicates some of the primary light 126 into photonic device 170 disposed proximate to optical loop 114 as a result of optical coupling between optical loop 110 and photonic device 170. Panel A of FIG. 13 shows microfabricated optical probe 100 and photonic device 170 at first separation distance D1 being optically under coupled to produce transmission spectrum shown in panel B, wherein the transmission spectrum has a maximum intensity modulation 1-I1. Panel C of FIG. 13 shows microfabricated optical probe 100 and photonic device 170 at second separation distance D2 being optimally optically coupled to produce transmission spectrum shown in panel D, wherein D1 is greater than D2, and the transmission spectrum has a maximum intensity modulation 1-I2 that is larger than 1-I1. Panel E of FIG. 13 shows microfabricated optical probe 100 and photonic device 170 in contact and optically over coupled to produce transmission spectrum shown in panel F, wherein the intensity modulation 1-I3 is smaller than 1-I2. Panel G shows cantilever 118 and optical loop 110 flexed with respect to substrate 120 on which microfabricated optical probe 118 and optical loop 110 are disposed. Flexing of cantilever 118 and optical loop 110 can occur due to contact of optical loop 110 with an object such as photonic device 170. It should be appreciated that cantilever 118 and optical waveguide 114 are flexible so that when cantilever 118 and optical loop 110 flex, cantilever 118 and optical loop 110 return to a non-flexed position shown in dashed lines in panel G. In this manner, cantilever 118 mechanically reversibly deforms in response to mechanical contact between optical loop 110 and photonic device 170.

In microfabricated optical probe 100, substrate 120 provides a mechanical foundation for cantilever 118 and optical waveguide 114. Exemplary materials for substrate 120 include a semiconductor such as silicon, GaAs, InP; glass, sapphire, silicon carbide, ceramic, or a combination thereof. In an embodiment, substrate 120 includes single crystal silicon. Additionally, the thickness of the substrate may be from 10 micrometers to 3 mm, specifically from 100 micrometers to 1 mm, more specifically from 400 micrometers to 700 micrometers. In an embodiment it is 500 micrometers. Additionally, the size of the substrate may be from 0.5 mm by 0.5 mm to 2 cm by 2 cm, specifically from 1 mm by 2 mm to 5 mm by 10 mm, more specifically from 1 mm by 3 mm to 5 mm by 5 mm. In an embodiment, it is 1.5 mm by 3.5 mm Cantilever 118 is disposed on substrate 120 and provides flexible mechanical support for the optical loop 110. The cantilever flexes in response to the waveguide loop 110 coming in contact with an external device. The flexing of the cantilever can be detected by a laser deflection technique. Exemplary materials for cantilever 118 include a semiconductor such as silicon, polycrystalline silicon, silicon carbide, GaAs, AlGaAs, InP, AlN; a piezoelectric such as PZT; a dielectric, such as silicon nitride, glass, silicon dioxide, sapphire, diamond; a polymer, or a combination thereof. In an embodiment, cantilever 118 includes single crystal silicon. Additionally, the cantilever thickness can be from 10 nm to 100 micrometer, specifically 100 nm to 10 micrometer, more specifically 250 nm to 3 micrometer. In an embodiment, the cantilever thickness of 260 nm.

Optical waveguide 114 is disposed on substrate 120 and provides optical communication between single mode optical fibers 124 and optical loop 110. It also provides flexible mechanical support to optical loop 110. Exemplary materials for optical waveguide 114 include a semiconductor such as silicon, polycrystalline silicon, silicon carbide, GaAs, AlGaAs, InP, AlN; a dielectric, such as silicon nitride, high-index glass, doped silicon dioxide, sapphire, diamond; a high-index polymer, or a combination thereof In an embodiment, optical waveguide 114 includes single crystal silicon.

Mechanical support 112 is interposed and interconnects cantilever 118 and optical waveguide 114 to provide mechanical support to the waveguide loop 110 and mechanical communication between waveguide loop 110 and cantilever 118. Exemplary materials for mechanical support 112 include a semiconductor such as silicon, polycrystalline silicon, silicon carbide, GaAs, AlGaAs, InP, AlN; a dielectric, such as silicon nitride, glass, silicon dioxide, sapphire, diamond; a polymer or a combination thereof. In an embodiment, mechanical support 112 includes single crystal silicon. Additionally, the width and geometry of the mechanical support 112 minimizes scattering of light from the waveguide 114. In an embodiment, the mechanical support is 100 nm wide and 260 nm thick.

Optical cladding layers 122, 132 are disposed on substrate 120 and provides optically isolate the waveguide 114, minimizing optical losses for light propagating in the waveguide 114. Exemplary materials for optical cladding layers 122, 132 independently include a semiconductor such as GaAs, AlGaAs, InP, AlN; a dielectric, such as silicon nitride, glass, silicon dioxide, sapphire, diamond; a polymer, or a combination thereof. In an embodiment, optical cladding layer 122, 132 independently include silicon dioxide.

Cover layer 130 is disposed on substrate 120 and provides protection and hard mask for selective removal of the cladding layers during fabrication. In an embodiment it provides additional mechanical support to cantilever 118. In an embodiment, it is flexible. Exemplary materials for cover layer 130 include a semiconductor such as silicon, polycrystalline silicon, GaAs, AlGaAs, InP, AlN; a dielectric, such as silicon nitride, glass, silicon dioxide, sapphire, diamond; a polymer, or a combination thereof. In an embodiment, cover layer 130 includes silicon nitride.

Pedestal 140 is interposed between cantilever 118 and cover layer 130 to provide mechanical attachment therebetween. Exemplary materials for pedestal 140 include a semiconductor such as silicon, polycrystalline silicon, GaAs, AlGaAs, InP, AlN; a dielectric, such as silicon nitride, glass, silicon dioxide, sapphire, diamond; a polymer, or a combination thereof. In an embodiment, pedestal 140 includes silicon nitride.

Optical fiber 124 is disposed on substrate 120 and provides optical communication between an external apparatus and waveguide 114. Optical fiber 124 transmits primary light from external apparatus to waveguide 114 and transmits output light to external apparatus with low optical loss. Exemplary materials for optical fiber 124 include glass, doped glass, or a combination thereof. In an embodiment, optical fiber 124 includes glass. In an embodiment, optical fiber 124 is standard commercial optical fiber designed for fiber telecommunications applications.

Figure 14:
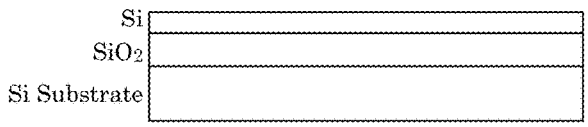
FIG. 14 shows steps in a process for making a microfabricated optical probe.
Figure 14:
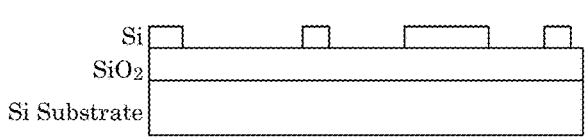
Figure 14:
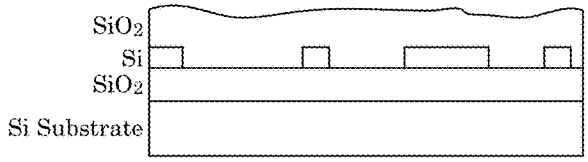
Figure 14:
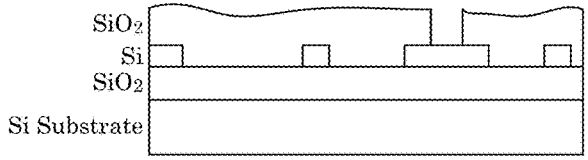
Figure 14:
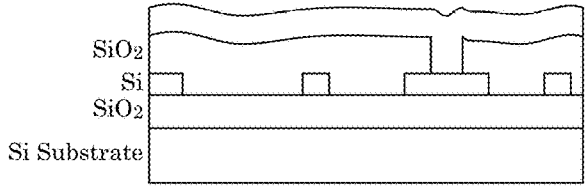
Figure 15:
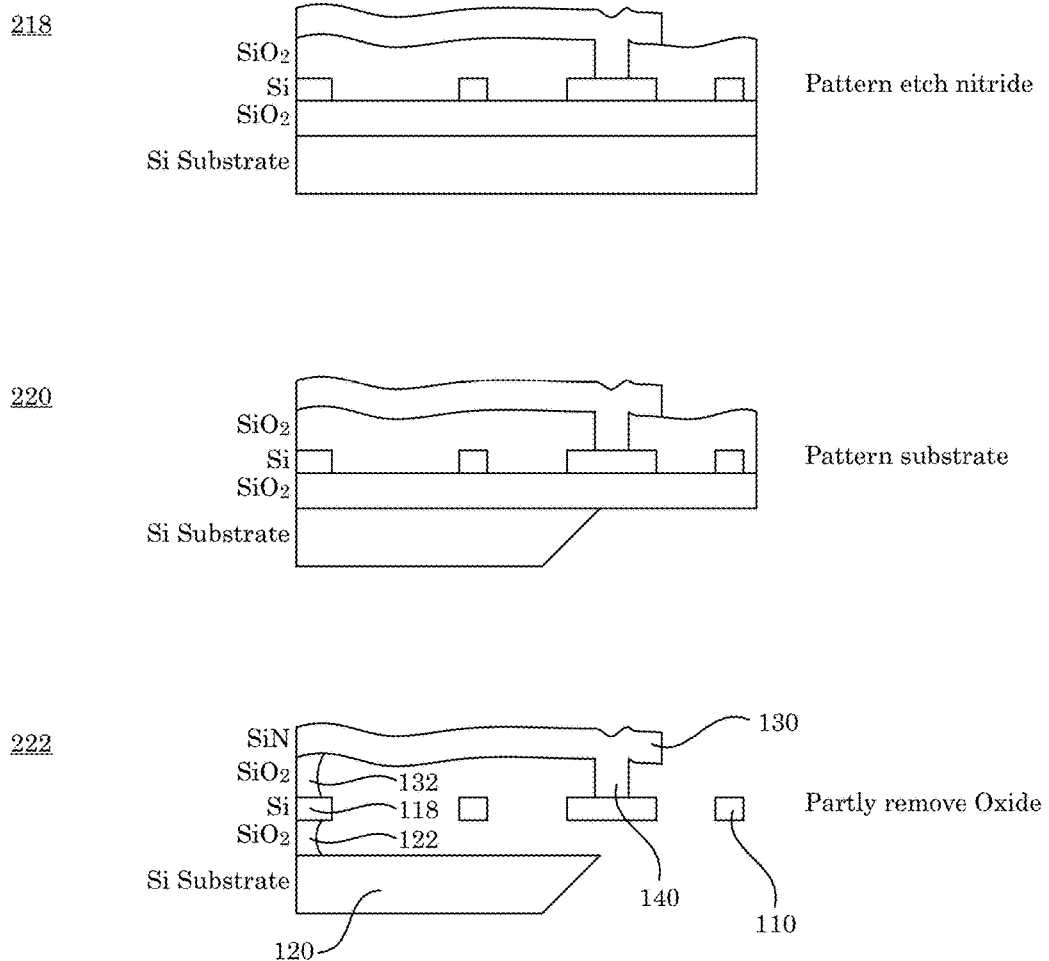
FIG. 15 shows steps in a process for making a microfabricated optical probe.

In an embodiment, with reference to FIG. 14 and FIG. 15, a process for making microfabricated optical probe 100 includes providing substrate 120 (step 210), wherein a layer of silicon dioxide or silicon can be disposed thereon as in a silicon on insulator wafer; defining features in the silicon layer, e.g., via lithography, etching, and the like (step 212); depositing an oxide on the silicon layer (step 213); patterning and etching holes in the oxide layer (step 214); depositing in nitride conformably to form a connection to silicon through the holes (step 216); patterning and etching the nitride layer (step 218); patterning substrate 120 (step 220); and partially removing the oxide to form microfabricated optical probe 100 (step 222).

According to an embodiment, a process for optically probing a photonic device includes approaching the loop 110 to the device at a predetermined location; detecting cantilever 118 deflecting as a result of mechanical contact with the device; retracting the probe to the desired separation for efficient optical coupling to the device; supplying primary light; detecting and analyzing secondary light. Additionally, it may include scanning the probe above the device, and energizing the device electrically and optically.

Microfabricated optical probe 100 and processes herein have numerous advantageous and unexpected properties. Unexpectedly, the structured region 111 allows changing the optical properties of the loop. In one embodiment, the effective index of the loop can be tuned to match the effective index of a high index photonic waveguide present in a device 170, and this allows for coupling of primary light 126 to such waveguide and efficient coupling of light from the device 170 to the output light 128. One advantage of this probe is the ability to use an appropriate tapered width of structured region 111 to tune the effective refractive index of the loop 110 to be higher than the refractive index of a cladding material used in the device 170, such as glass, and therefore minimize scattering of primary and output light into the cladding layer of the device.

Another unexpected advantage of the probe 100 is the ability to form an optical resonator in the structured region 111 by forming a Bragg grating with a defect or forming a photonic crystal resonator in the structured region 111. This allows to strongly enhance the optical coupling to and from device 170 at a specific desired optical frequency.

Another advantage is the ability to detect mechanical contact based on the deflection of the cantilever 118. This allows integration of the optical probe with commercial and custom scanning probe instruments that have the ability to measure cantilever deflection and position and control cantilever to device separation accurately based on that.

The articles and processes herein are illustrated further by the following Examples, which is non-limiting.

EXAMPLES

Example 1. Optical Probe for Nondestructive Wafer-Scale Characterization of Photonic Elements This Example describes fabrication and operation of a microfabricated optical probe for nondestructive evanescent coupling and localized testing of nanophotonic devices and circuits. A microfabricated silicon (Si) waveguide ($\approx$300 nm$\times$$\approx$260 nm cross section) loop forming a $\approx$10 µm diameter half-circle is suspended in air at the tip of a cantilever extending from a single-mode fiber-connectorized silicon on insulator chip ($\approx$1.5 mm$\times$$\approx$3.5 mm). The microfabricated optical probe can be used in commercial scanning probe microscopes (SPM) for accurate positioning, controlled optical coupling, and chip-scale and wafer-scale testing. We demonstrate this by performing spectroscopy on a Si microdisk optical cavity with an optical quality factor of $\approx$10$^6$. The SPM enables precise measurement and stable control of sample-probe distance to vary the coupling rate from under- to over-coupled regimes.

The automated non-destructive electrical testing of devices during the fabrication greatly increases the yield through statistical process control and reduces costs by selecting "known good die" for further processing and packaging, essential for microelectronic manufacturing. Similar testing is desirable for integrated photonic devices in research and manufacturing. Traditional optical coupling methods, including fiber-end coupling and prism-based coupling require packaging before testing. Incorporating fixed grating couplers for chip and wafer-scale non-destructive testing consumes precious circuit area and provides only fixed levels of optical coupling at pre-specified locations. The microfabricated optical probe provides variable, controlled and directional coupling of light immediately into and out of unmodified waveguides or photonic devices.

Conventional fiber-taper probes include a single mode fiber that is locally stretched, creating a waist of a few hundred nanometer in diameter, and enabling evanescent coupling. While Conventional fiber-taper probes have low optical loss, high bandwidth and fine polarization control, the resulting thin fiber section is soft and subject to low frequency mechanical noise, complicating control over the coupling depth. Shaping such probes to access specific locations on a dense photonic circuit with sizeable surface topography is difficult, requires artisanal fabrication techniques, and the resulting bend radius is still large.

The small and stiff microfabricated optical probe reported here is immune to low frequency mechanical vibration. The microfabricated optical probe is disposed at the end of a micromechanical cantilever and used in a commercial SPM system to control the microfabricated optical probe-sample separation and the evanescent coupling rate. Furthermore, the Si probe's effective index can be set by choosing the waveguide width, with the highest index approaching that of bulk Si. Effective index matching to the device under test increases coupling. Choosing a high effective index allows index matching for deeper coupling to otherwise inaccessible high-index modes in non-undercut Si and SiN cavities and waveguides. It also avoids optical losses into their lower index $SiO_2$ cladding layers.

Figure 16:
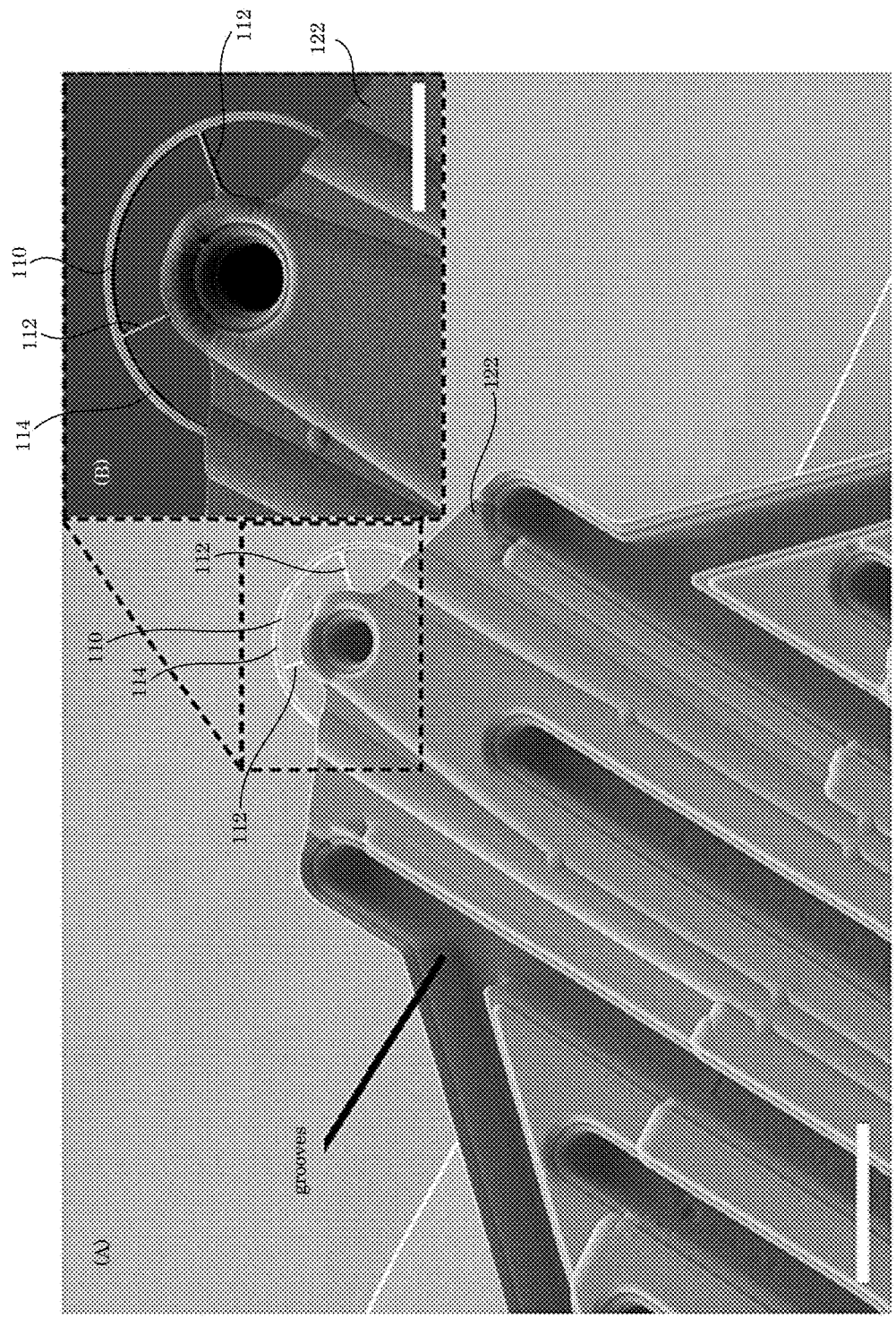
FIG. 16 shows a false-color scanning electron micrograph of a release of an optical probe. Light blue is Si, green is SiN. Si waveguide loop is supported by additional tethers and attached to the cantilever, which is formed by a combination of SiN and SOI layers. Grooves visible in the SiN structures increase structural rigidity of the cantilever and attach it to the Si substrate (light blue on the left and right of the cantilever). Scale bars are (a) 10 μm and (b) 5 μm.

A fully integrated, fiber pigtailed microfabricated optical provides for operating in the telecommunication wavelength range ($\approx$1550 nm) (FIG. 16). The microfabricated optical probe was fabricated using a custom wafer-scale batch fabrication process. One electron beam patterning, four i-line stepper, and two contact mask aligner lithography steps are used to define photonic structures in the Si device layer and mechanical structures in SiN. Silicon dioxide ($SiO_2$) serves as sacrificial layer and waveguide cladding. Si has high refractive index for simpler matching to Si photonic devices. Alternatively, a SiN photonic layer may be used for applications in the visible. The SOI layer is nominally 260 nm thick and the nominally 500 nm wide on-chip waveguide is tapered down to a minimum width of $\approx$300 nm where it forms a half-circle loop, extending the evanescent field into the surrounding air (FIG. 16b)). A SiN cantilever structure is used to mechanically support the extending Si waveguide loop. A pattern of deep "anchor" groves is dry-etched through the $SiO_2$ and SOI before conformal SiN deposition. These anchors attach the nitride and SOI structures to the substrate and to each other for mechanical rigidity, which increase the resonance frequency of the cantilever structure up to $\approx$8 MHz. Anisotropic Si etching is used to form fiber attachment V-grooves and to partly remove the handle Si wafer to overhang the cantilever. The sacrificial $SiO_2$ layers are removed by an isotropic timed etch in hydrofluoric acid, exposing the loop.

Figure 17:
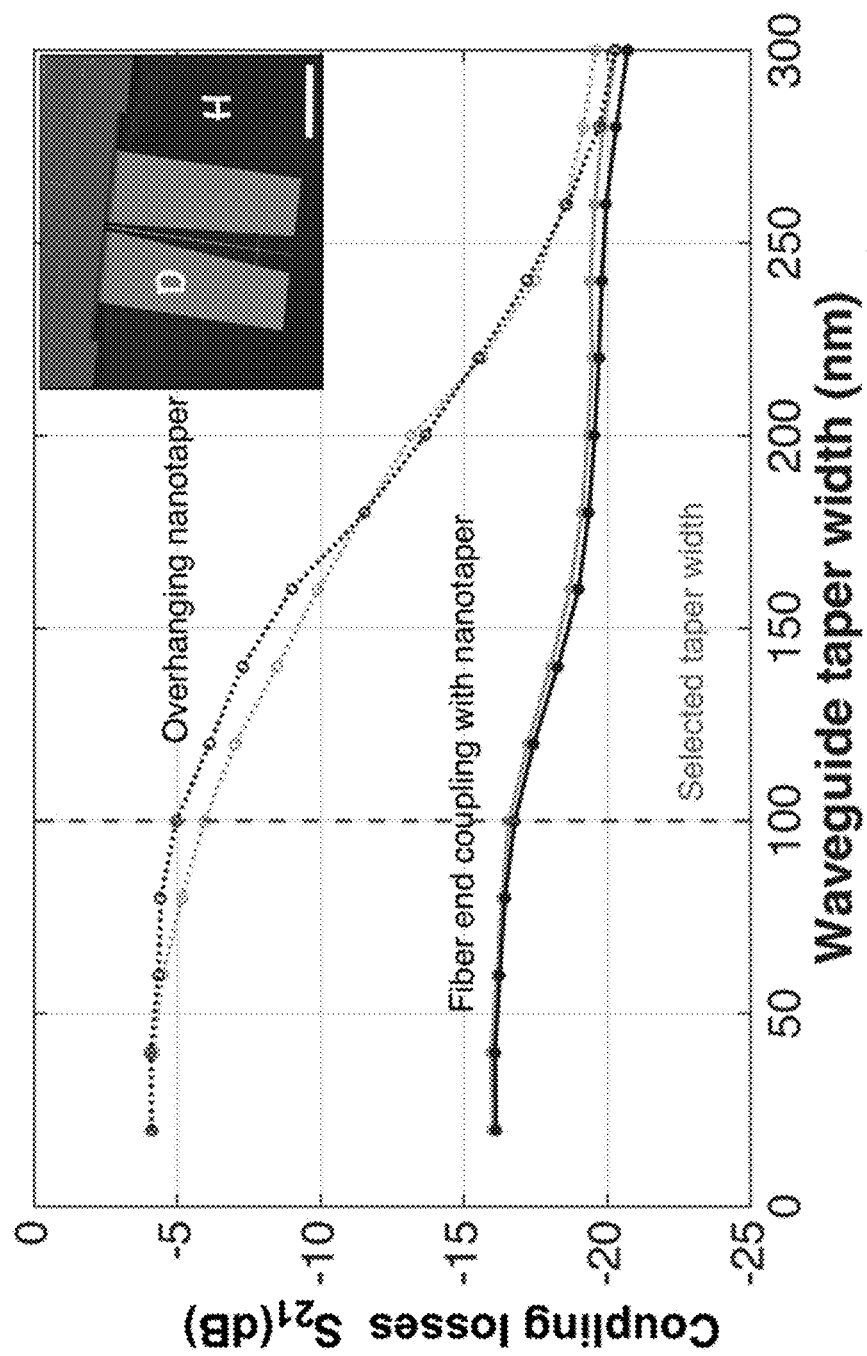
FIG. 17 shows a simulation result of the transmission (S21) as a function of taper width. The uniform taper length is 50 μm. The graph shows the fiber to Si waveguide transmission FEM results for the released, air-cladding nanotaper (dotted line) as well as for an $SiO_2$-cladding nanotaper, with 2 μm buried $SiO_2$ separating waveguide from the Si handle wafer (solid line). The red color represents the results for the TM mode and blue for the TE mode. The inset shows the colorized SEM micrograph of a fabricated air-cladding nanotaper after the release (white scale bar corresponds to 20 μm). The D and H in the inset, mark the Si device layer and Si handle wafer respectively.

The microfabricated optical probe is fiber-pigtailed by placing standard cleaved single-mode optical fibers into $\approx$1.3 mm long on-chip V-grooves. Fibers are actively aligned and permanently attached using a UV curable adhesive. The $\approx$50 µm end sections of the SOI waveguides are inverse-tapered to expand the optical mode for low loss coupling, and suspended in air at the V-groove ends. They are held in place by narrow crossbars attached to larger suspended Si "flag" structures on both sides (FIG. 17 inset).

Minimizing optical loss is important for many applications of the microfabricated optical probe. Alternative approaches for fiber connectorizing such devices have to be weighed carefully. In our case robustness and small size were major considerations, dictating the choice of end-fire coupling with fibers parallel to the chip surface, as opposed to the grating coupler geometries with fibers near-normal to the chip surface. The coupling loss achieved between the on-chip waveguide and the optical fiber is $\approx$5.5 dB per facet, in line with numerical predictions (FIG. 17). The limited thickness of bottom oxide cladding ($\approx$2 µm) further dictated the need to suspend the inverse taper to avoid losses into the substrate. Simulations for the coupling efficiency with fiber end-fire coupling in the presence of the $SiO_2$ cladding and Si substrate showed much lower coupling efficiency, because of high optical losses into the Si handle wafer (FIG. 17). For further reduction of optical losses, the coupling between a fiber, which is tapered down to a narrow tip, can lay on top of the waveguide to reach a high efficiency. Another approach for coupling is including a lensed fiber array to couple to the chip.

Figure 18:
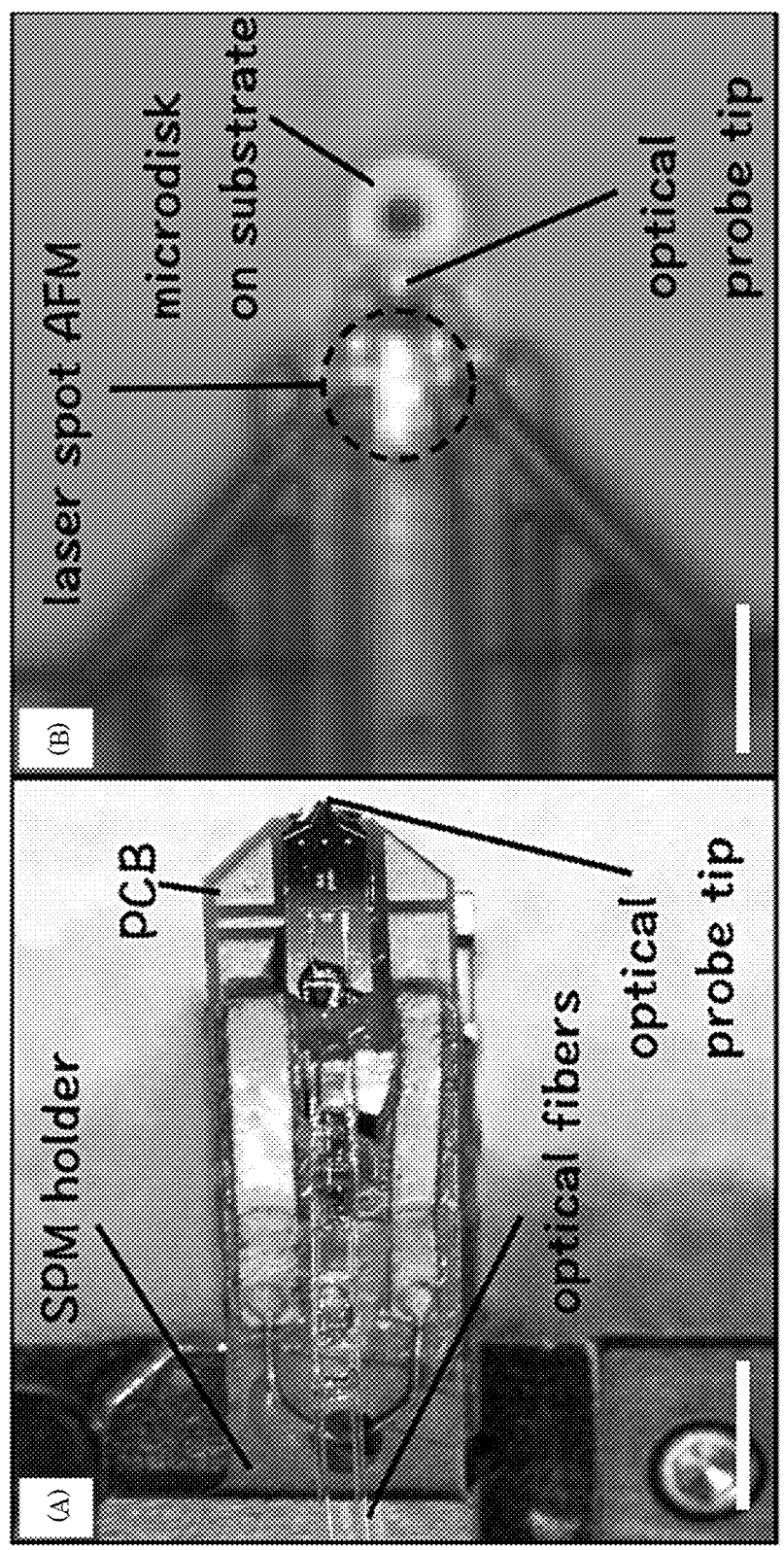
FIG. 18 shows (a) the 1.5 mm by 4.5 mm Si chip (green) with the microfabricated optical probe at the tip and optical fibers coming out of the V-grooves on the back. The chip and fibers are physically attached to a printed circuit board (PCB, golden) adaptor held in a commercial SPM holder, and panel (b) shows the SPM camera view of the Si microdisk (bright green) fabricated on a silicon substrate (light blue) being approached and probed by the optical probe (green). The laser spot of the beam deflection detection system of the SPM is visible on the microfabricated optical probe's cantilever. Scale bars are (a) 4 mm, and (b) 20 μm.
Figure 19:
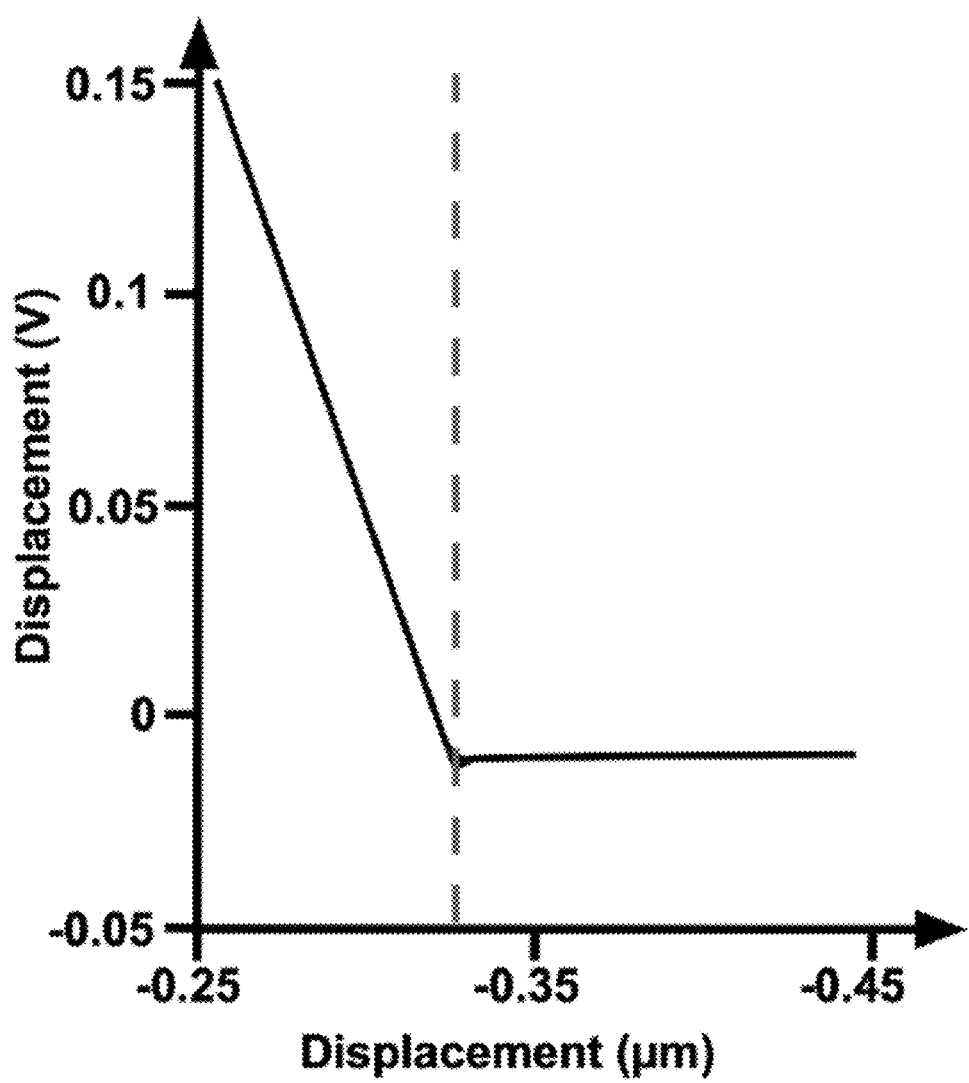
FIG. 19 shows a force curve of the cantilever, used to detect the microfabricated optical probe-sample physical contact point. The calibrated Z-piezo of the SPM is then used to make the measurement at the desired probe-sample separation. The dashed green line indicates the position of the sample surface.

The microfabricated optical probe was used to conduct swept-wavelength optical spectroscopy on a Si microdisk high Q optical cavity. The optical probe is mounted in the cantilever holder of the scanning probe microscope (SPM) (FIG. 18(a)). The laser of the SPM beam deflection detection system is focused on the SiN cantilever structure, as shown in FIG. 18(b). To set the optical probe height relative to the device under test, a force curve was recorded by moving the microfabricated optical probe toward the sample and recording the SPM beam deflection signal (FIG. 19). The force curve is a plot of the deflection of the cantilever versus the extension of the piezoelectric scanner in z, measured using a position sensitive photodetector. At small separations, the microfabricated optical probe comes in contact with the surface and the increased cantilever deflection is a linear function of distance. The onset of cantilever deflection marks the point of contact between the microfabricated optical probe and the sample. We can then use the calibrated, close-loop controlled actuation of the SPM to achieve a desired probe-sample separation.

Optical spectroscopy measurements are based on a tunable (≈1520 nm to ≈1570 nm) fiber-coupled diode laser. Light from a laser is sent through a fiber polarization controller and coupled into the microfabricated optical probe device input fiber. Polarization is manually adjusted to maximize the evanescent coupling to the photonic structure under investigation. Light intensity from the output fiber is measured with a photodetector. The laser wavelength is swept and the transmission spectrum is recorded, revealing the spectral location and spectral width of the optical cavity modes. Optical power into the microfabricated optical probe was approximately 0.08 mW.

Figure 20:
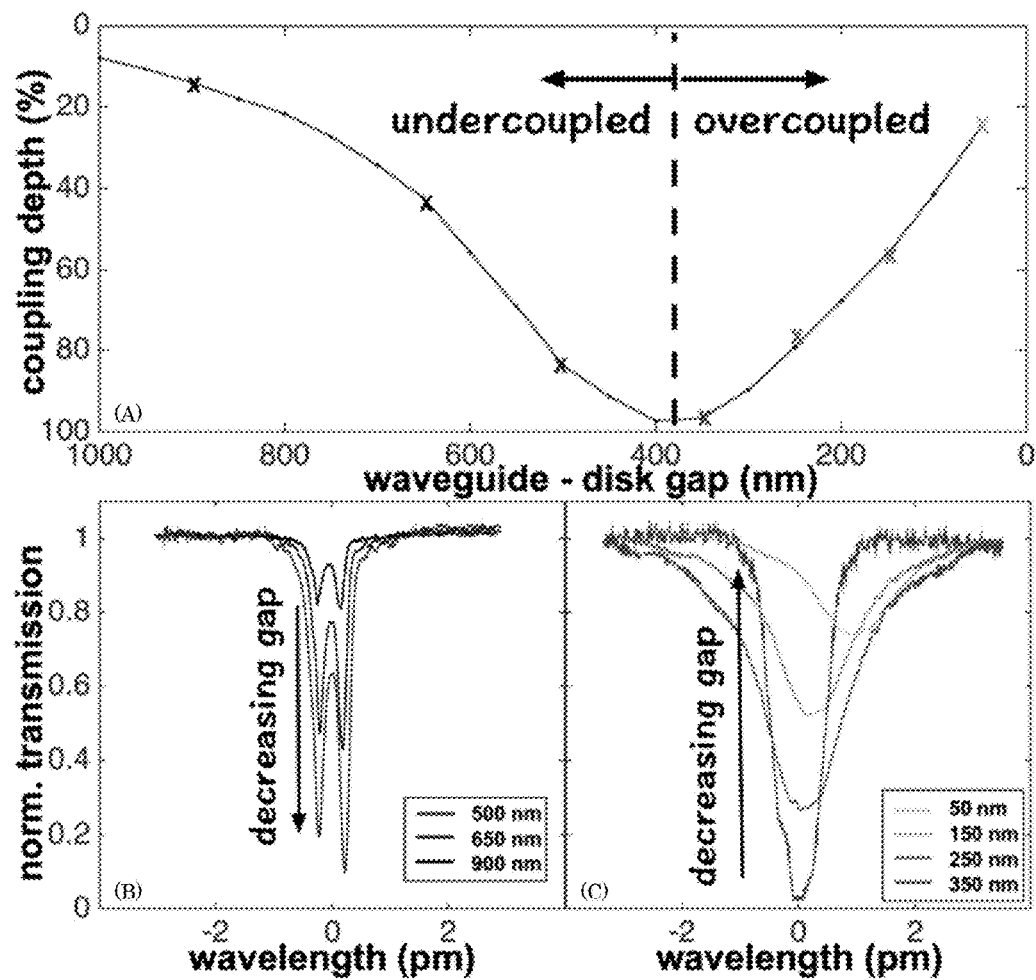
FIG. 20 shows spectroscopy of a 10 μm diameter, 260 nm thick Si microdisk optical cavity using the optical probe. Absorption feature from a transverse magnetic (TM) whispering gallery mode is centered at 1540.35 nm. (a) Coupling depth as a function of probe-disk spacing with under coupled and over coupled regions highlighted. (b) Selected transmission scans taken from the under coupled and over coupled regime, as indicated by colored crosses in a). Intrinsic quality factor of Q of $10^6$ and doublet splitting of 0.1 GHz are evident from the under coupled spectra. Based on repeated measurements, the one standard deviation statistical uncertainty is smaller than the data makers. b) shows the spectrum for a gap of 900 nm, 650 nm, and 500 nm. c) shows the spectrum for a gap of 350 nm, 250 nm 150 nm, and 50 nm.

We measured a Si micro disk with a diameter of ≈10 µm, anchored ≈2 µm above the surface of a Si wafer. The micro disk is fabricated from the ≈260 nm thick Si device layer of an SOI wafer and has an optical quality factor of ≈$10^6$. The SPM stage was used to position the disk edge under the microfabricated optical probe and the SPM height actuator was used to position the microfabricated optical probe in steps of ≈50 nm away from the Si micro disk to measure the spectra, revealing the change in optical coupling as a function of the microfabricated optical probe/disk gap. FIG. 20(a) plots the transmission contrast vs. disk-probe gap, and shows that critical coupling is achieved at ≈420 nm separation. Near 100% absorption by the cavity is reached, indicative of good polarization matching. FIG. 20(b)-(c) shows the spectral transmission dips corresponding to a first-radial order transverse magnetic mode of the micro disk for different disk/probe gaps.

While an SPM can achieve superior control and automation, for many research and testing applications the calibrated close-loop stage as well as the beam deflection detection system for the automated approach and close-loop control are not necessary. Here, the microfabricated optical probe can be used with a simpler micromanipulator and/or a probe station.

The microfabricated optical probe provided local, nondestructive testing of photonic structures and was microfabricated in a wafer scale batch-fabrication process. Accurate control over the optical coupling with a commercial scanning probe microscope has been demonstrated through spectroscopy of a high-quality factor Si micro disk photonic cavity.

Example 2. Fabrication Process for an Optomechanical Transducer Platform with Integrated Actuation This Example describes batch fabrication of a fiber pigtailed optomechanical transducer platform with an overhanging member. The platform provides a high bandwidth, high sensitivity, and highly integrated sensor that is compact and robust with the potential for low cost batch fabrication inherent in micro-opto-electro-mechanical-systems (MEMS) technology.

The fabrication process includes electron beam lithography, i-line stepper lithography, and back- and front-side mask aligner lithography. Moreover, this process makes use of equipment in nanofabrication facilities and research laboratories, facilitating broad adaptation and application of the process. Therefore, this process is useful for the nano- and microfabrication research communities at large.

An obstacle to realizing the potential of micro- and nanomechanical sensing is the readout of the motion of the small resonator with high sensitivity, high bandwidth, and without excess power dissipation. In the past years numerous methods for the readout of resonator motion have been developed. Electrical readout schemes, such as capacitive, magnetomotive, piezo-resistive, and piezoelectric are convenient but suffer from various combinations of poor scaling with reduced size, power dissipation limitations, magnetic field and material requirements, and thermal Johnson noise in the readout signal. On the other hand, optical readout schemes, such as beam deflection and interferometric, substitute optical shot noise for thermal noise, in principle don't dissipate any power at the transducer, and have a high measurement bandwidth. However, to effectively couple motion to light, most of the off-chip optical methods need a certain minimum moving structure size and reflectivity, which often involves bulky structures or mechanically dissipative reflective coatings.

Figure 21:
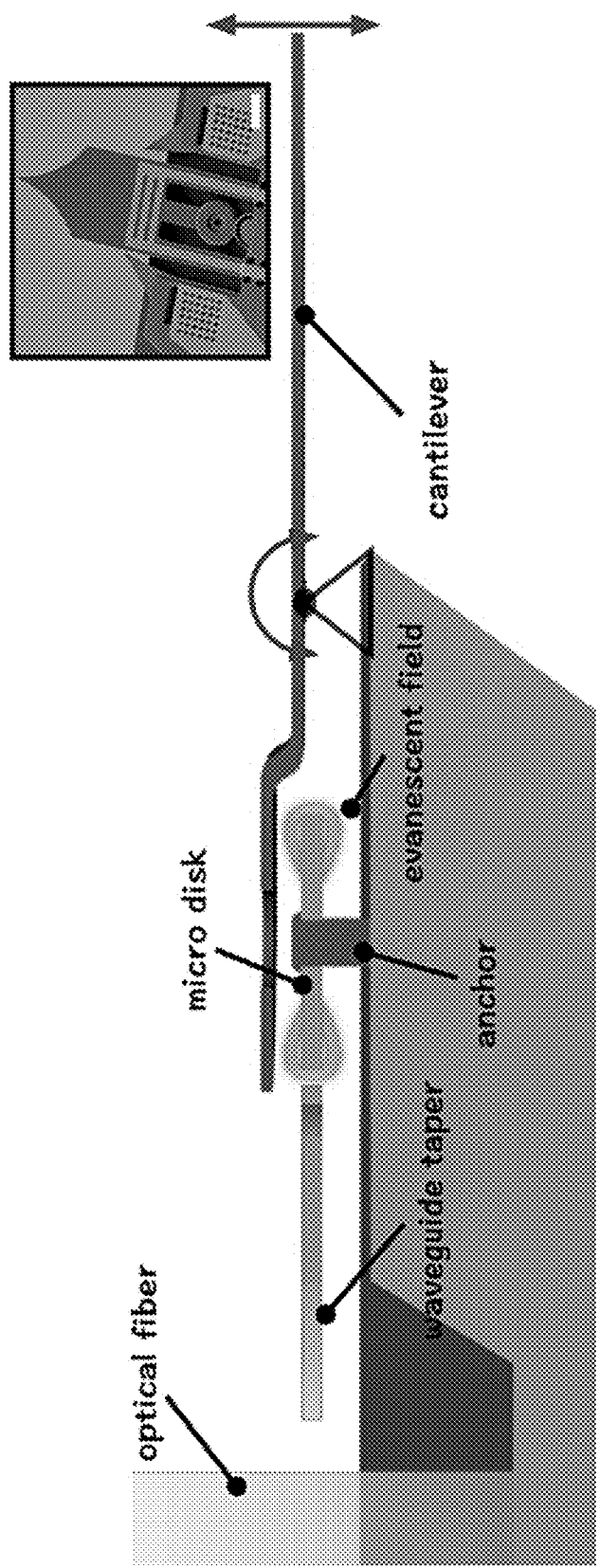
FIG. 21 shows an exemplary schematic of the transducer (not to scale) showing overhung cantilever on a torsional pivot as the mechanical device. SiN is shown in green, Si is shown in blue and grey. The red arrow indicates the direction of movement. (inset) False-color scanning electron micrograph of a released device after the fabrication process. Yellow represents metallization, green represents SiN, light blue represents the Si device layer, and dark blue represents the Si handle wafer. Scale bar is 10 µm.

In nanophotonic optical cavities, light is trapped in a very small volume and interacts for a longer time and more closely with the mechanical resonator. Typical photonic cavity optical quality factors on the order of $10^5$ to $10^6$ increase the readout signal-to-noise by the same factor. The readout bandwidth is reduced from ≈100 THz optical frequency to about ≈100 MHz, still fast enough for most mechanical sensors. Maintaining stable coupling of a microscopic mechanical resonator with an off-chip optical cavity is challenging due to alignment and drift of components with respect to each other. Here this challenge is overcome by integrating the high-quality factor optical cavity directly underneath the moving device, allowing strong interaction with the optical near-field of the cavity, while avoiding mechanical contact (FIG. 21). This interaction is described by the optomechanical coupling coefficient ($g_{OM}$ typically in the units of GHz/nm) relating the change in optical frequency of the micro disk cavity to the displacement of the mechanical device. This fully integrated stable and practical optomechanical transducer is fiber connectorized and implements the readout of mechanical motion with gigahertz bandwidth.

Low-loss, stable, and robust fiber coupling of the transducer provides sensitive and reliable operation. Therefore, the fibers are securely attached to the chip without excess losses between the on-chip waveguide and the optical fiber.

This readout approach provides independent tailoring of the various optical and mechanical parts of the transducer. The photonics can be separately optimized for low losses, high quality factor and desired cavity size, while tuning the waveguide-cavity coupling depth and the optomechanical coupling to achieve the optimal readout sensitivity and dynamic range. The mechanical components' size, shape, stiffness, and resonance frequency can be tailored to best address the specific sensing applications. The actuation can be tailored for the displacement and force ranges, ideally without introducing mechanical losses, avoiding increased mechanical noise and decreased Q in resonators.

Conventional devices focus on parts of a transducer, e.g., tuning of optical cavities coupling to optical chips, displacement measurement on moveable structures, or the fundamental physics of optical microdisk cavities. Here, a compact, robust fiber pigtailed optomechanical transducer platform is described, which is useful for the nanofabrication and nanophotonic research community, and process steps can be adapted for other fabrication projects.

FIG. 21 shows an arrangement of components in our transducer platform that includes an optical fiber, inverse-taper coupler, waveguides, microdisk cavity, and the mechanical (torsional cantilever) structure. Electrically-controlled actuators (not shown) are also included in the platform to tune the static position and dynamically excite the motion of the mechanical device.

The photonic structures for operation in the telecommunication wavelength range ($\approx$1550 nm) are fabricated in the silicon device layer of a silicon-on-insulator (SOI) wafer, because of the outstanding optical and mechanical properties of silicon. The mechanical device is created in silicon nitride (SiN), because it shows good mechanical properties resulting in high quality factor devices, has low optical loss, an index of refraction below that of Si and is compatible with a hydrofluoric (HF) acid release. For the metallization, we choose gold with a chromium adhesion layer (Cr/Au), compatible with HF and potassium hydroxide (KOH) etches. Furthermore, the combination of SiN and Cr/Au shows a good thermal bimorph actuation efficiency. Silicon dioxide is used as the sacrificial material.

The sensitivity to motion is proportional to the optical quality factor of the micro disk cavity and quickly increases with decreasing gap between the cavity and the mechanical resonator. It is therefore important to accurately locate the mechanical structure in close proximity to the optical micro disk cavity, while maintaining the high optical quality ($\approx 10^5$ to $\approx 10^6$) factor of the micro disk optical mode. In our design, the micro resonator is lithographically aligned to the disk, and completely encloses it, while a sacrificial layer defines the gap in the fabrication process. A dedicated lithography step and an etch step are used to reduce the sacrificial layer thickness to a predetermined value at the optomechanical transducer ($\approx$400 nm), allowing us to control the gap within tens of nanometers, while keeping a thicker silicon dioxide sacrificial and cladding layer elsewhere. The thickness has been determined with simulations and measurements. It is important that the gap between the silicon microdisk and the silicon nitride is not too small, to avoid excessive leakage form the optical mode into the silicon nitride layer. This would dramatically reduce the optical quality factor of the device. Furthermore, for some of the transducers presented in this paper, discussed in other papers, it is possible to tune the readout gain.

Figure 22:
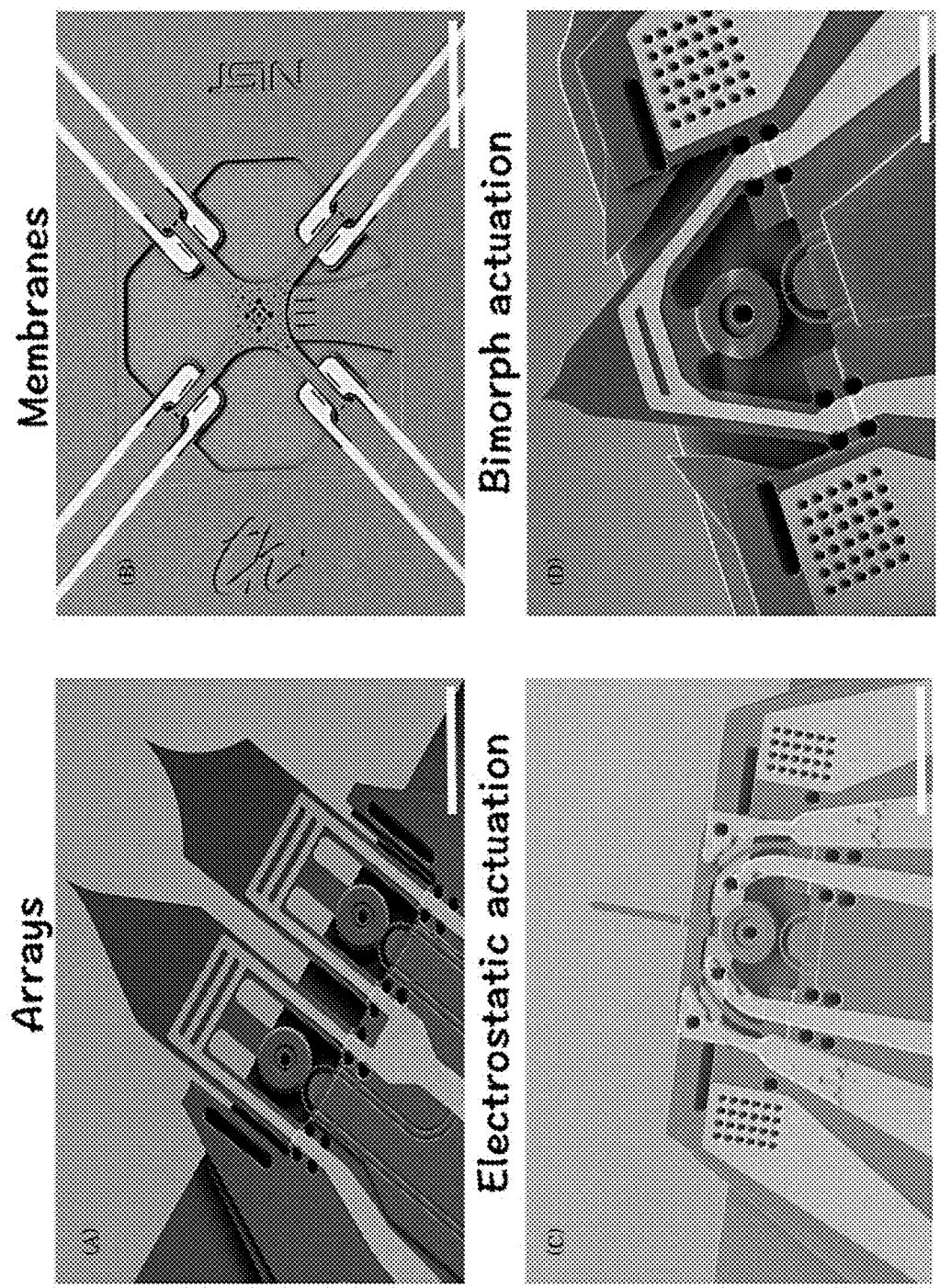
FIG. 22 shows designs of a process flow. The scale bars correspond to a) 20 µm, b) 100 µm, c) 30 µm, and d) 30 µm.

Separating photonic and mechanical layers affords flexibility in the design of the mechanical parts to suit specific sensing applications. Within the same process flow, we design and fabricate mechanical cantilever structures, torsional structures, and membranes, on chip structures, and overhanging structures, as well as various types of actuation mechanisms (FIG. 22). The transducer arrays can be used for the simultaneous high sensitivity force detection, such as in parallelized scanning probe microscopy. The membrane transducers show a high mechanical quality factor and good frequency stability, which can be used to study forces acting on samples attached to the membrane. Four different designs of the membrane transducer are designed to have resonance frequencies between $\approx$70 kHz and $\approx$2 MHz. The two different option for excitation of the photonic probes allow to design probes with a high-quality factor and stable resonance frequency as well as probes with tunable readout gain. The cantilever probes show resonance frequencies between $\approx$50 kHz and $\approx$2 MHz for the first eigenmode.

The integration of an actuator increases the range of possible applications. The built-in static actuation allows tuning the transducer gain and measurement range. This is accomplished by changing the static gap size between the mechanical structure and the optical cavity. We decided to develop designs for two actuation schemes, thermal bimorph and electrostatic actuation. Bimorph actuators deliver fast responses and large forces. However, the introduction of metal on the mechanical structure creates significant internal losses and therefore reduces the mechanical quality factor. In contrast, electrostatic fringe field actuation does not involve metal in contact with the mechanical member, which lets the mechanical member freely oscillate and does not affect the mechanical quality factor. This commonly used type of actuation enables measurements on dielectric resonators, where useful electrostatic forces for frequency tuning and motion excitation are applied directly to the dielectric structure, thus avoiding any unwanted degradation of the mechanical quality factor.

The devices were fabricated in a unified batch fabrication process and a single platform, which can be tailored for specific applications. In the following we will present the process using the overhanging cantilever probe.

Figure 23:
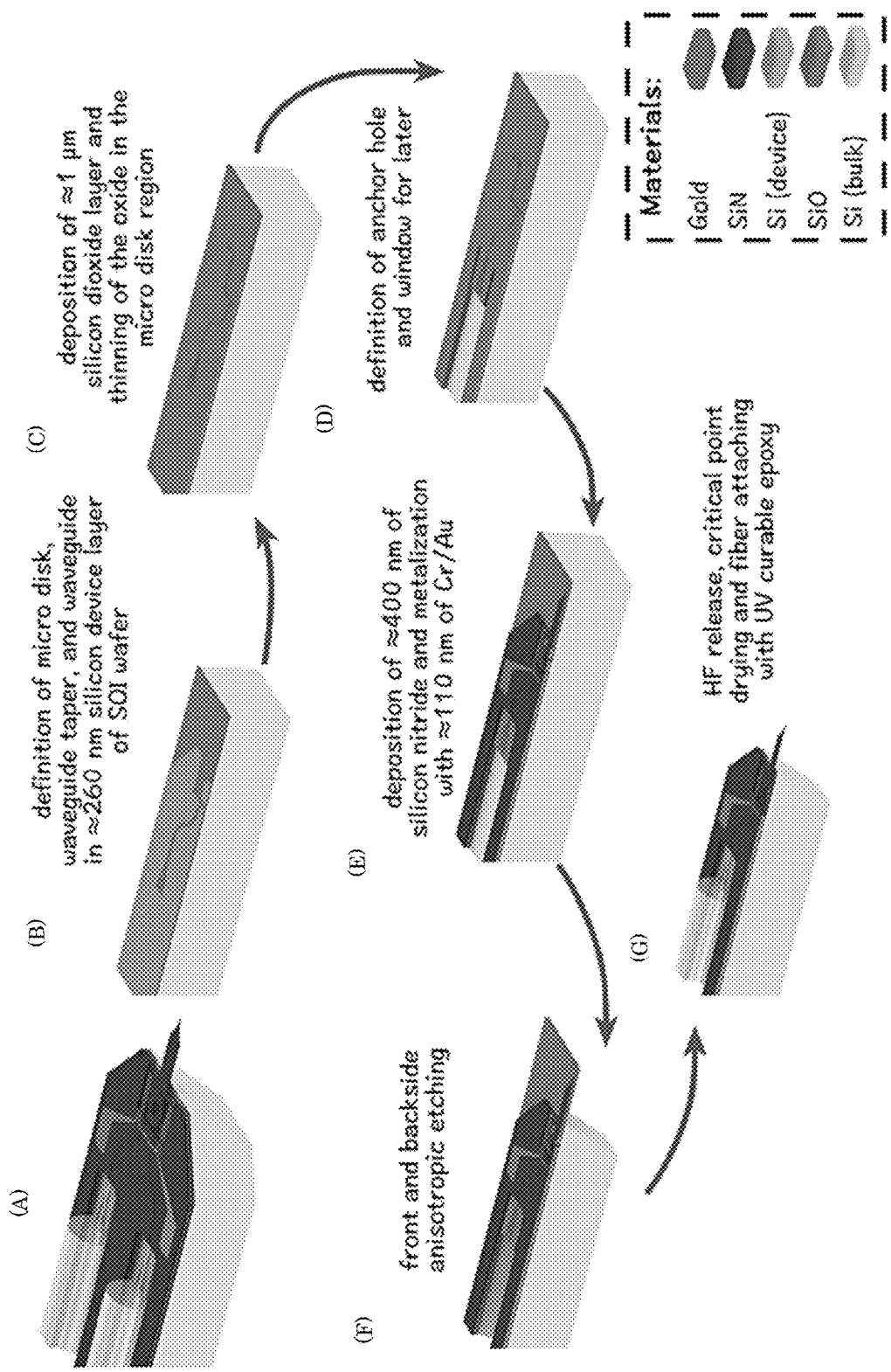
FIG. 23 shows a process flow for the transducer with integrated thermal actuation and overhanging tip. The image in the top left shows the finished device (a). (b) Definition of micro disk, waveguide taper, and waveguide in ≈260 nm silicon device layer of SOI wafer. (c) Deposition of ≈1 µm silicon dioxide layer in micro disk region. (d) Definition of anchor hole and window for later V-groove etching. (e) Deposition of ≈400 nm of silicon nitride and metallization with ≈110 nm of Cr/Au. (f) Front and backside anisotropic etching. (g) HF release, critical point drying and fiber attaching with UV curable epoxy.

The fabrication of the cavity optical transducer is based on double-side polished SOI. The process flow is summarized in FIG. 23 In the first step, the waveguide taper, waveguide, and micro disk are defined via electron beam lithography and inductively-coupled reactive ion etching (RIE) of the SOI device layer down to the buried oxide layer (BOX). The nominal width of the waveguide is $\approx$500 nm and the gap between the waveguide and the disc is defined to be $\approx$340 nm. Both waveguide ends are linearly tapered down to a width of $\approx$100 nm over the distance of $\approx$50 μm for low loss coupling to/from optical fibers ($\approx$5.5 dB per facet) (FIG. 23b). The remaining structures are defined by i-line stepper optical lithography unless otherwise noted. A sacrificial silicon dioxide layer ($\approx$1 μm) is deposited in a low-pressure chemical-vapor deposition furnace (LPCVD) and defined to create a window to the Si substrate for the later KOH etching as well as a hole in the center of the micro disk, which is used to anchor the micro disk to the bulk silicon with the following SiN layer. The silicon dioxide is thinned down by a $CF_4$ plasma etch through a lithographically-defined window in photoresist in the region above the micro disk to ensure good optomechanical coupling (FIG. 23c, d). The optomechanical coupling for these devices is $\approx$26 GHz/nm. A low-stress silicon nitride layer ($\approx$400 nm) deposited with LPCVD acts as a passivation layer in the waveguide region and as a structural material for the mechanical structure. Following nitride deposition, a gold layer is deposited and defined in a liftoff process to create a micro heater, electrical connection, and wire bond pads. For the electrostatically actuated transducer, the micro heater is replaced by electrodes for fringe field actuation. The SiN layer is lithographically patterned (FIG. 23e), and dry etched to form the SiN cantilever, SiN ring above the micro disk, and SiN anchor to mechanically attach the micro disk to the bulk silicon. The previously defined metal layer is used as a hard mask for SiN, to self-align the SiN structure in critical areas (FIG. 23e). For front side protection during the later KOH etch, a hafnium oxide (HfO) layer is deposited with atomic layer deposition. In the following, a RIE is used to open up a window in the HfO and SiN for anisotropic etching of the silicon, and to form v-grooves for optical fibers. A back to front aligned backside lithography followed by RIE etching is used to form an anisotropic etch window on the backside as well. Both lithographies for the definition of the front and back side etch window for anisotropic etching are defined with contact aligner lithography. During the anisotropic silicon etch, V-grooves are formed on the front side of the chip and the shape of the cantilever chip is defined by etching through the handle wafer from the backside (FIG. 23e). Another approach is the replacement of the backside KOH etch with an ICP etch to create a backside trench with vertical sidewalls. This approach is currently being used to develop acceleration sensors with large seismic masses made from the handle wafer.

Silicon dioxide layers and HfO are removed by 49% HF wet etching to undercut and release the movable structures as well as the micro disk, which is anchored to the bulk silicon with a SiN anchor. A critical point drying process is used to avoid stiction between the parts due to capillary forces (FIG. 23f). At the end of each v-groove the overhanging waveguide inverse tapers are suspended between silicon support structures and coupled to optical fibers. Which are placed in the V-groove, actively aligned and glued into place with ultraviolet (UV) light curable epoxy.

The described fabrication process is based on a 100 mm SOI wafer. The device layer thickness of the wafer is ≈260 nm with low doping to insure good optical transmission. The buried oxide layer has a thickness of ≈2 μm, which is important to prevent leakage of the optical energy in the guided mode from the photonic structure into the silicon handle wafer. The crystal orientation in the handle wafer and the device layer is (100) which results in the desired V-groove and cantilever chip shape after the anisotropic etching.

For backside polishing, the fabrication starts with polishing the backside of the SOI wafer for better control of the anisotropic backside etching as one of the final fabrication steps. The polishing is achieved with a table-top chemical-mechanicals-polishing system (CMP). For the protection of the front side of the wafer during the polishing process, a combination of a silicon dioxide hard mask and a soft mask created with photoresist is used. The hard mask is created with a flowable oxide (i.e., FOX 16). The flowable oxide is based on an inorganic polymer in a methyl isobutyl ketone (MIBK) carrier solvent, the solvent volatilizes rapidly from the resin, leaving a planar surface. The soft mask consists of a thick photoresist mask.

For cleaning: the wafer is cleaned with N-Methyl-2-pyrrolidone (Resist remover 1165) at ≈70° C. for ≈15 min, followed by a rinse with isopropyl alcohol and blow dry with nitrogen gun. Alternatively, the wafer can be dried in the spin dryer and is useful for batch fabrication runs with more than one wafer.

For frontside protection including a hard mask, "FOX 16" diluted ≈1:10 with MIBK is used for the hard mask; the FOX is applied with the following spin coater setting of ≈10.47 rad/s (≈100 rpm) for ≈5 s followed by ≈314.16 rad/s (≈3000 rpm) for ≈40 s, and the mask is cured in three consecutive soft bake steps to prevent the layer from cracking. Starting with ≈90° C. for ≈1 min, followed by ≈180° C. for ≈1 min, and ≈400° C. for ≈1 min, resulting in a cured thickness of ≈400 nm.

For frontside protection a soft mask is used in which: the soft mask is created with a thick photo resist layer ("AZ 10xT") with the following spin coater parameter of ≈10.47 rad/s (≈100 rpm) for ≈5 s followed by ≈209.44 rad/s (≈2000 rpm) for ≈45 s, and the polymer layer is cured in a soft bake step of ≈115° C. for ≈10 min, resulting in a cured thickness of ≈12 μm.

For chemical mechanical polishing (CMP), a slurry solution based on colloidal silica ("Ultra-Sol 556") diluted with deionized water in a ratio of ≈4:10 is used for the polishing process; the process steps for the conditioning of the system are summarized below, and for the conditioning of the polishing pad, the "Conditioner" is lowered on our CMP system. The conditioning step is used to break in the polishing pad for reproducible results. The steps and conditions are as follows Step #1
Time: 5 min
Force: 2.5 kg
Pump #1: 0 ml/min (Slurry)
Pump #2: 40 ml/min (H$_2$O)
Pad: ≈4.7 rad/s (≈45 rpm) (CW)
Wafer: 0 rad/s (0 rpm)
Slider: 50 mm to 70 mm (5 min$^{-1}$)
Step #2
Time: 5 min
Force: 2.5 kg
Pump #1: 50 ml/min (Slurry)
Pump #2: 0 ml/min (H$_2$O)
Pad: ≈4.7 rad/s (≈45 rpm) (CW)
Wafer: 0 rad/s (0 rpm)
Slider: 50 mm to 70 mm (5 min$^{-1}$)

After conditioning, the conditioner is raised to allow the wafer/polishing pad contact; the following parameters are chosen to polish the backside of the wafer down to a polished surface. This polishing step removes ≈20 μm of material on the rough wafer backside of a single-side polished wafer.

Step #1
Time: 1 min
Wafer: 100 mm
Force: 17.236 kN/m$^2$
Pump #1: 20 ml/min (Slurry)
Pump #2: 0 ml/min (H$_2$O)
Pad: ≈3.66 rad/s (≈35 rpm) (CW)
Wafer: ≈3.14 rad/s (≈30 rpm) (CCW)
Slider: 50 mm to 70 mm (10 min$^{-1}$)
Step #2
Time: 2 h+30 min
Wafer: 100 mm
Force: 45.642 kN/m$^2$
Pump #1: 20 ml/min (Slurry)
Pump #2: 0 ml/min (H$_2$O)
Pad: ≈3.66 rad/s (≈35 rpm) (CW)
Wafer: ≈3.14 rad/s (≈30 rpm) (CCW)
Slider: 50 mm to 70 mm (10 min$^{-1}$)
Step #3
Time: 15 min
Wafer: 100 mm
Force: 3.447 kN/m$^2$
Pump #1: 0 ml/min (Slurry)
Pump #2: 50 ml/min (H$_2$O)

Pad: ≈3.66 rad/s (≈35 rpm) (CW)
Wafer: ≈3.14 rad/s (≈30 rpm) (CCW)
Slider: 50 mm to 70 mm (5 min$^{-1}$)

The slurry should not sit on the wafer for a long time after the polishing finished because the slurry will attack the surface. To avoid an attack of the surface, the wafer is rinsed thoroughly with DI water right after the polishing to remove all slurry residues and dried with nitrogen.

For cleaning, the wafer is cleaned with N-Methyl-2-pyrrolidone (Resist remover 1165) at ≈70° C. for ≈15 min, followed by a rinse with isopropyl alcohol and deionized water DI water (DIW) dump rinse; buffered oxide etch (16% BOE) is used for the removal of the hard mask. This etch is performed in cycles of 30 s of etching and a DI water dump rinse until the silicon surface is hydrophobic. This step takes ≈1 min for the described oxide thickness. Before the start of the patterning processes, the wafer is cleaned using the Radio Corporation of America cleaning (RCA clean). Table 1 lists the parameters for cleaning.

TABLE 1

| RCA I | |
|---|---|
| Solution: | DIW/NH$_4$OH/H$_2$O$_2$(50 ml/10 ml/10 ml) |
| Time: | ≈10 min |
| Temperature: | ≈75° C. |
| HF dip | |
| Solution: | HF/DIW (2 ml/100 ml) |
| Time: | ≈30 s |
| Temperature: | room temperature (RT) |
| RCA II | |
| Solution: | DIW/HCl/H$_2$O$_2$(50 ml/10 ml/10 ml) |
| Time: | ≈10 min |
| Temperature: | ≈75° C. |

For this step, the wafer was placed in a 100-mm cassette for the handling; add the hydrogen peroxide only a few minutes before the cleaning; otherwise, the hydrogen peroxide will be consumed by the bath before the actual cleaning. The hydrogen peroxide for RCA II should not be added earlier then ≈7 min before the bath is used.

The wafers are dump rinsed between every step. After the last cleaning bath, the wafers are dried in the spin dryer. A good test during the cleaning is to check the hydrophobicity of the silicon surface after the HF dip. The surface should be hydrophobic, if this is not the case, the HF dip should be repeated.

Alignment marks were made according to the following step that includes electron beam lithography. We use the flat of the wafer to align the wafer to the electron beam lithography layer to the crystallographic orientation of the silicon wafer. For the alignment of the electron beam lithography, we create alignment marks with a contact mask aligner and a silicon etch on the wafer. We then use these alignment marks to actively align the lithography pattern written by the electron beam system to the crystal orientation of the wafer. The alignment marks are also used for drift check during the electron beam write, to minimize stitching between the write fields. The depth of these alignment marks is very important to create a mark with good contrast in the electron beam tool. The alignment marks are lithographically defined in an i-line stepper lithography.

For lithography, hexamethyldiloxane is used for the preparation of the wafer surface to improve the adhesion between resist and wafer surface; the wafer is heated up in a vacuum furnace to ≈120° C.; after a short bake-out (≈20 min), Hexamethyldiloxane vapor is flowed into the chamber for the deposition, followed by a couple of purge cycles to remove the Hexamethyldiloxane from the chamber prior to venting to atmosphere; a standard positive photoresist is used for this lithography process ("S1813"), and the resist layer is applied in a spin coating process, with the following spin speed parameters of ≈10.47 rad/s (≈100 rpm) for ≈5 s followed by ≈418.88 rad/s (≈4000 rpm) for ≈45 s (final resist layer thickness ≈800 nm). The resist is soft baked at ≈115° C. for ≈1 min. The wafer is exposed with 140 mJ/cm$^2$ (I-line 365 nm) at 365 nm with a focus of 0 μm, numerical aperture of 0.6, and a sigma of 0.7 in the "annular" illumination mode.

For pattern transfer, the structure is transferred with a parallel plate reactive ion etcher; the silicon device layer is etched with a sulfur hexafluoride chemistry, followed by an etch based on fluorocarbon chemistry for the silicon oxide layer (the BOX layer of the SOI wafer), and the parameters of the etch are summarized in Table 2.

TABLE 2

| Si Etch | |
|---|---|
| Tool: | RIE #2 |
| Time: | 3 min |
| Gases: | SF6/CF4 |
| Flow rates: | ≈6 mL/min (≈6 sccm)/≈24 mL/min (≈24 sccm) |
| Pressure: | ≈1 Pa (8 mTorr) |
| RF power: | ≈200 W |
| Ref. RF power: | ≈0 W |
| DC Bias: | ≈516 V |
| Etch rate: | ≈100 nm/min |
| SiO$_2$ etch | |
| Tool: | RIE #2 |
| Time: | 12 min |
| Gases: | O2/CHF3 |
| Flow rates: | 5 mL/min (5 sccm)/45 mL/min (45 sccm) |
| Pressure: | 6.7 Pa (50 mTorr) |
| RF power: | 200 W |
| Ref. RF power: | ≈0 W |
| DC Bias: | ≈516 V |
| Etch rate: | ≈35 nm/min |

The depth of the final marks was more than 750 nm to be clearly visible in the electron beam lithography system.

For cleaning, after the dry etch, the wafer is cleaned in a piranha solution (H$_2$SO$_4$:H$_2$O$_2$) to remove the resist as well as the polymers which have been created during the etch process. A piranha solution with the ratio H$_2$SO$_4$:H$_2$O$_2$ (3:1) is used. The wafers are placed in the fresh solution for ≈10 min, followed by a dump rinse and spin dry.

For electron beam lithography, this step defines the photonic structures in the silicon device layer. The nominal width of the final waveguide is ≈500 nm and the gap between the waveguide and the disk is defined to be ≈340 nm. The waveguide is linearly tapered down to a width of ≈100 nm over the distance of ≈50 μm at both waveguide ends for low loss coupling to optical fibers. All dimensions are positively biased by 10 nm for the electron beam lithography to take dimension change due to oxidation into account. We use the electron beam resist "ZEP 520A" with a base dose of ≈460 μC. The base dose is modulated to compensate proximity effects in the lithography process, which is critical for the disk/waveguide gap as well as for the waveguide taper width. Small variations in these dimensions have a significant effect on the optical device performance. The electron beam lithography is performed on a gaussian beam electron beam system with a write field of 1 mm$^2$.

The structures are written with "floating" write fields to optimize the lithography results. "Floating" fields are primarily used to eliminate stitching in critical areas. Floating field pattern fracturing forces the field stitch boundaries to known areas, which are typically chosen to contain straight sections of a waveguide. Additionally, the layout and pattern conversion are optimized to reduce the writing time between consecutive fields containing stitched elements. This reduces any drift induced stitching errors. The resist is developed with hexyl acetate at ≈0° C. to improve the contrast, followed by a transfer step for the generated pattern into the silicon device layer. We transfer the pattern with a hydrogen bromide and chlorine chemistry (HBr/$Cl_2$). This etch was chosen as it is known to be a highly anisotropic silicon etch with good control over the sidewall angle. HBr also produces fewer defects in the surface. Alternatively, we tried a pseudo gas-chopping approach with a plasma chemistry based on octafluorocyclobutane and sulfur hexaflouride ($C_4F_8$/$SF_6$). The lithography step combined with the transfer into the silicon device layer is a critical step in this fabrication process, since a small deviation in the created lateral device dimension can have a significant influence on the optical performance of the devices.

For the electron beam lithography, the resist "ZEP 520A" is used because of its good selectivity in our silicon etch process (An alternative product is "CSAR62"). The resist is applied with a spin coater and the following spin speeds of ≈10.47 rad/s (≈100 rpm) for ≈5 s followed by ≈366.52 rad/s (≈3500 rpm) for ≈35 s, which results in a final layer thickness of ≈400 nm). The resist is soft baked at ≈180° C. for ≈2 min. To minimize charging effects during the electron beam lithography, a thin charge dissipation layer based on ≈15 nm of aluminum is used. This thin metal layer has a negligible influence on the electron beam resolution but shows a sufficient conductivity to reduce charging of the resist. Furthermore, aluminum can be easily removed with tetramethylammonium hydroxide (TMAH) based developer after the exposure. The aluminum layer is applied via thermal evaporation. The evaporation with a source based on electron beam heating might affect the resist properties due to unwanted exposure to electron beams.

For the exposure of the prepared wafer, an electron beam lithography tool is used, with a base dose of ≈460 μC. After the exposure, the aluminum layer is removed in TMAH based developer ("MF319") for less than 1 min. Shortly after dipping the exposed sample into the developer, the exposed area will appear in the aluminum layer, before the aluminum layer starts to disappear. The wafer is rinsed with DIW to remove residuals of the developer and dried with nitrogen. The wafer electron beam resist is developed in hexyl acetate at ≈0° C. to improve the contrast. A cooling plate based on Peltier elements is used to achieve a sufficient temperature control. The development in cold hexyl acetate takes ≈120 s. The wafer is removed from the developer and dried with nitrogen immediately to remove developer residuals. Alternatively, the wafer can be rinsed with MIBK and isopropyl alcohol (IPA) before dying. However, MIBK can create cracks in "ZEP 520A" with a thickness of more than about ≈400 nm.

Before the pattern can be transferred into the silicon device layer, the chamber is conditioned for the etch chemistry. Depending on the starting conditions, this sometimes takes more time than mentioned in this recipe. The conditioning starts with a bare 100 mm silicon wafer, which is etched for ≈20 min. After the etching, the wafer surface should be shiny and not dark black. The shiny surface is a good indicator that the chamber is clean and in reasonable condition. A black surface indicates the creation of black silicon on the wafer, which is an indicator that the chamber condition is not ideal. Table 3 provides the conditions for conditioning.

TABLE 3

| Tool: | Plasma etcher |
|---|---|
| Time: | ≈20 min |
| Substrate: | ≈100 mm silicon wafer |
| Gases: | HBr/$Cl_2$ |
| Flow rates: | ≈10 ml/min (≈10 sccm)/≈5 ml/min (≈5 sccm) |
| ICP power: | ≈700 W |
| Ref. ICP power: | ≈6 W |
| RF power: | ≈60 W |
| Ref. RF power: | ≈1 W |
| Pressure: | ≈2 Pa (≈15 mTorr) |
| Temperature: | ≈20° C. |
| Helium backing: | ≈2.6 Pa (≈20 Torr) |
| DC Bias: | ≈155 V |

The conditioning with the bare silicon wafer is followed by a silicon wafer with resist pattern. The exposed silicon area of this wafer is approximately the area which will be etched on the process wafer as well. The only difference is, that this is a bare silicon wafer with a resist mask created via stepper lithography, to create waveguide structures for visual inspection of the etch results. Further conditioning parameters are included in Table 4.

TABLE 4

| Tool: | Plasma etcher |
|---|---|
| Time: | ≈2 min 30 s |
| Substrate: | ≈100 mm silicon wafer with resist mask |
| Gases: | HBr/$Cl_2$ |
| Flow rates: | ≈10 ml/min (≈10 sccm)/≈5 ml/min (≈5 sccm) |
| ICP power: | ≈700 W |
| Ref. ICP power: | ≈6 W |
| RF power: | ≈60 W |
| Ref. RF power: | ≈1 W |
| Pressure: | ≈2 Pa (≈15 mTorr) |
| Temperature: | ≈20° C. |
| Helium backing: | ≈2.6 Pa (≈20 Torr) |
| DC Bias: | ≈142 V |

The etch results are inspected in the scanning electron microscope to determine the sidewall angle, etch rate, and uniformity across the wafer. Typical sidewall angles are between ≈90' and ≈87°. The typical etch rate is ≈95 nm/min with an etch rate uniformity of ±5 nm in lateral dimension. The sidewall angle can be adjusted with the process pressure. The test etch is repeated until the desired etch profile is reached. Pattern transfer conditions are listed in Table 5.

TABLE 5

| Tool: | Plasma etcher |
|---|---|
| Time: | adjusted with results from test etch |
| Substrate: | ≈100 mm SOI wafer with ZEP 520A |
| Gases: | HBr/$Cl_2$ |
| Flow rates: | ≈10 ml/min (≈10 sccm)/≈5 ml/min (≈5 sccm) |
| ICP power: | ≈700 W |
| Ref. ICP power: | ≈6 W |
| RF power: | ≈60 W |
| Ref. RF power: | ≈1 W |
| Pressure: | ≈2 Pa (≈15 mTorr) |
| Temperature: | ≈20° C. |

TABLE 5-continued

| | |
|---|---|
| Helium backing: | ≈2.6 Pa (≈20 Torr) |
| DC Bias: | ≈142 V |

The structure is over etched to create vertical sidewalls across the whole wafer und compensate for possible non-uniformities in the vertical etch rate. The displayed DC Bias will change if the surface of the buried oxide layer is reached. The etch rate of the resist is ≈72 nm/min. An over etch into the BOX layer is acceptable as the etch rate on silicon oxide is ≈50 times higher than that of silicon.

Another commonly used etch chemistry for photonic structures is an ICP etch based on sulfur hexafluoride and octafluorocyclobutane. In contrast to the standard gas chopping process, where these gases are used in alternating steps of "etching" (sulfur hexafluoride) and "passivating" (octafluorocyclobutane), they are used simultaneously instead to create very smooth sidewalls. However, this simultaneous etching and passivation makes the process difficult to use because of a small process window for a stable etch. The rate at which the passivation is deposited on the side wall and bottom of the trench strongly depends on the chamber conditions, i.e., polymers build-up on the chamber walls. We were able to realize devices with similar optical quality factors with this etch chemistry. However, the process strongly depends on the etch load and the chamber conditions and therefore has to be adjusted for every sample. This makes this etch preparation very time consuming. Furthermore, this etch is very sensitive to over etching. During an over-etch, BOX layer will charge up, which creates a deflection of the ions at the bottom. These defected ions etch the sidewall passivation and create notching.

In contrast to this, an over-etch with the HBr chemistry does not create notching because the anisotropic properties of the etch are not created by a side wall passivation. The vertical side walls depend on the directional kinetic energy of the HBr radicals. The etch is based on the amorphization effect of $Cl_2$ and HBr on silicon.

The wafer is cleaned with a combination of solvents to remove the plasma baked resist after the etching. In the first step, a solvent based on N-Methylpyrrolidone and N-(2-Hydroxyethyl)-2-Pyrrolidone ("EKC-Remover") at ≈70° C. for ≈10 min, followed by a dump rinse and spin dry. Piranha solution ($H_2SO_2:H_2O_2$) is used to remove the bulk polymer in a ratio of $H_2SO_2:H_2O_2$ (3:1) for ≈10 min followed by a dump rinse and spin dry.

The electron beam lithography is followed by an i-line stepper lithography to define larger-area structures in the silicon device layer. This step defines a trench around the cantilever chip and removes the silicon device layer below the future cantilever structure. The stepper lithography uses a standard positive photoresist and is followed by an inductive plasma etch process to transfer the structure into the silicon. The HBr chemistry has been chosen for this step because of the high etch selectivity between silicon and silicon dioxide. The stepper lithography and the earlier electron beam lithography overlap in certain areas to create continuous regions with removed silicon. The high etch selectivity reduces the step between the two areas, which is created in the this etch process.

The wafer is exposed with 140 mJ/cm², a focus of 0 µm, a numerical aperture of 0.6, and a sigma of 0.7 in the "angular" illumination mode. The pattern is developed in "MF 319" for ≈60 s followed by a DIW rinse and dried with nitrogen.

The pattern is transferred with the HBr recipe described above. Table 6 provides pattern transfer conditions.

TABLE 6

| | |
|---|---|
| Recipe: | Plasma etcher |
| Time: | adjusted with results from test etch |
| Substrate: | ≈100 mm SOI wafer with resist mask |
| Gases: | HBr/$Cl_2$ |
| Flow rates: | ≈10 ml/min (≈10 sccm)/≈5 ml/min (≈5 sccm) |
| ICP power: | ≈700 W |
| Ref. ICP power: | ≈6 W |
| RF power: | ≈60 W |
| Ref. RF power: | ≈1 W |
| Pressure: | ≈2 Pa (≈15 mTorr) |
| Temperature: | ≈20° C. |
| Helium backing: | ≈2.6 Pa (≈20 Torr) |
| DC Bias: | ≈142 V |

The structure is over etched by 10% to ensure uniform results.

The wafer is cleaned with piranha solution ($H_2SO_2:H_2O_2$) to remove the bulk polymer as well as etch residuals. A ratio of $H_2SO_2:H_2O_2$ (3:1) is used for ≈10 min.

For waveguide cladding and spacer layer, the waveguide cladding layer consists of silicon dioxide. The cladding is created in a thermal oxidation and a chemical vapor deposition (CVD) step where low temperature oxide (LTO) is deposited. A first thermal oxidation step is used to clean the silicon surface from any contamination, as well as defects created during the silicon etch. This clean will also remove the halogenated and amphorizied surface layer, which has been created by $Cl_2$ and HBr during the silicon etch. The created oxide is removed with a wet oxide etch followed by a second thermal oxidation. The second thermal oxidation creates a good interface layer between the silicon crystal and the silicon dioxide layer created by CVD. Unfortunately, the thickness of the oxide layer created by our deposition tool has a non-uniformity of ±10%. To reduce the influence on the deposited layer, the deposition process is split into three separate depositions. The wafer is turned between the depositions by ≈120°. After the first LTO deposition, the layer is etched back with a silicon dioxide dry etch to prevent the creation of encapsulated cavities in the oxide due to the growth dynamics of the CVD process. The dry etch is based on a tetrafluoromethane ($CF_4$) chemistry, because this chemistry creates fewer etch residuals. This is important to avoid any contaminations of the cladding layer. This step is followed by two LTO depositions and a high temperature anneal in a nitrogen atmosphere. The annealing process drives the hydrogen out of the layer and improves the mechanical, electrical, optical, and chemical (etch rate) properties. The $N_2$ atmosphere prevents a further oxidation of the silicon device layer.

Before the deposition of the cladding layer, the wafer is cleaned with a RCA clean. The wafer is cleaned.

For thermal oxidation, the SOI wafer is placed with one clean bare monitor silicon wafer on each side in the furnace boat. The monitor wafers are used to determine the grown silicon dioxide thickness after the run. The wafers are dry oxidized at ≈1000° C. for ≈10 min, which will create an oxide thickness of ≈12 nm. Therefore, the original silicon surface is moved ≈5 nm into the silicon, since the volume of thermal oxide consists out of ≈44% silicon. The wafers are removed from the furnace and the oxide is stripped in diluted HF (≈2%), followed by a dump rinse and spin dry. The wafer is etched in diluted HF until the surface is hydrophobic. The thermal oxidation can be repeated with the same or similar parameters For LTO deposition or for the CVD deposition, we determined the deposition rate with a full wafer boat and on the wafers in the center of the boat. The non-uniformity in this process between wafers can be significant. The wafers in the center are in general more uniform then wafers on the sides of the boat. The SOI wafer is placed in the center of the boat with one clean monitor silicon wafer on each side. The monitor wafers are used to determine the grown silicon dioxide thickness after the run. The deposition is performed at ≈400° C. for ≈400 nm. The wafers are removed and etched in a parallel plate reactive ion etcher, the parameters are listed in Table 7.

TABLE 7

| Tool: | RIE Unaxis 790 |
|---|---|
| Depth: | ≈200 nm |
| Gases: | O2/CF4 |
| Flow rates: | ≈5 sccm/≈25 sccm |
| Pressure: | ≈6.7 Pa (≈50 mTorr) |
| RF power: | ≈200 W |

After the etch back, the wafers are loaded into the CVD furnace for the next LTO deposition. The deposition is again performed at ≈400° C. for ≈400 nm. The wafers are rotated to improve the uniformity of the deposition, followed by the last deposition. The deposition is performed at ≈400° C. for ≈600 nm. After the final deposition, the wafers should have a final silicon dioxide thickness of ≈1.2 μm. To finish up the LTO deposition, the wafers are annealed at ≈1000° C. in a $N_2$ atmosphere for ≈1 h. The annealing process drives the hydrogen out of the layer and improves the mechanical, electrical, optical, and chemical (etch rate) properties. The $N_2$ atmosphere is very important to prevent a further oxidation of the silicon device layer.

Figure 24:
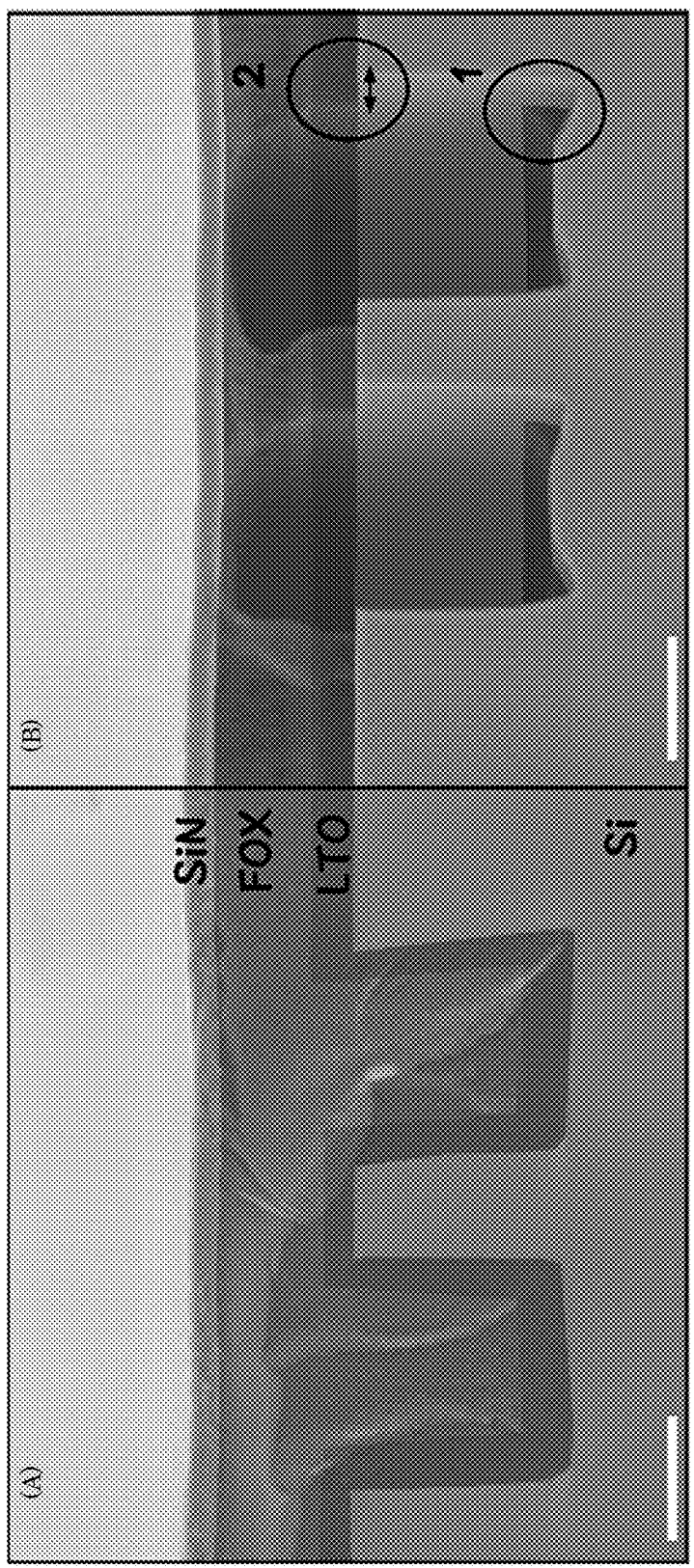
FIG. 24 shows a cross sectional view of a test sample before (a) and after (b) the exposure to HF. The red circle in #1 points out that there is still LTO left in the corners of the trench, which shows that the lateral etch rate of the LTO is lower compared to the lateral etch rate of FOX in the trench. However, circle #2 shows that the lateral etch rates for both layers (LTO and FOX) are comparable outside the trench. This indicates that the high internal stress of the FOX layer in the trench has an influence on the lateral etch rate. The scale bars correspond to 400 µm.
Figure 25:
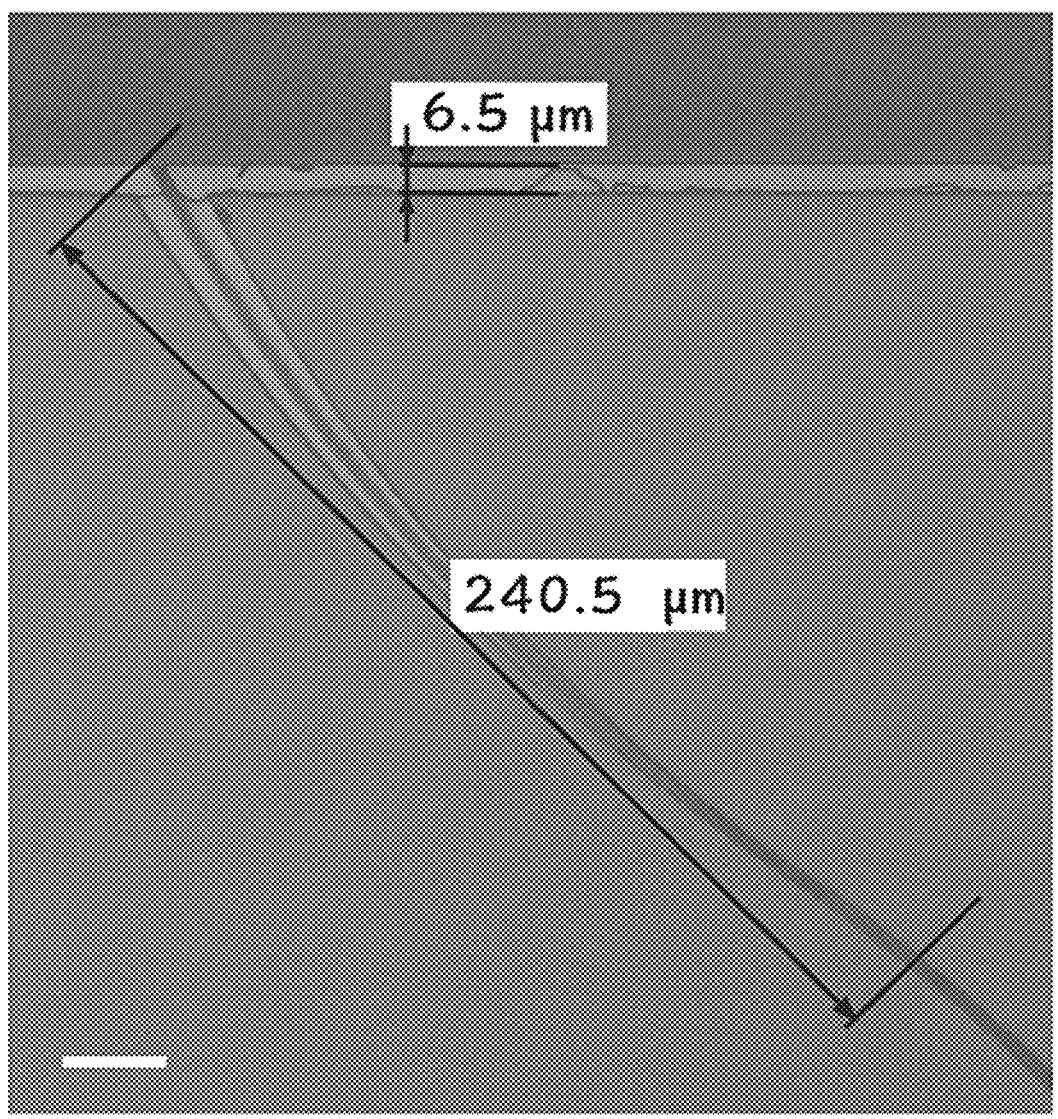
FIG. 25 shows a top view of a cleaved test sample after the sample was exposed to HF for several minutes. The test sample consists of an SOI wafer structured with a waveguide. The waveguide structure is covered with a layer of LTO, FOX, and SiN. The images show a difference of lateral etch rate.

As alternate approach to creating a cladding, use FOX as described previously for the polishing hard mask. The advantage of FOX is the outstanding planarization capability, which will level all topographical steps and therefore simplify the lithographies for the following fabrication steps. In addition, the processing time for FOX compared to the LTO deposition is lower and less expensive. FOX is applied in a spin coating process and soft baked on a hot plate, followed by a rapid thermal annealing (RTA) and a 1 h annealing in a nitrogen atmosphere. However, we observed problems with FOX as waveguide cladding for this process. The silicon waveguide is defined by a trench, with an aspect ratio of (1:2), on each side. In test experiments, we cured the FOX layer with different temperatures and atmospheres and were able to create a planar layer without any visible defects or cracks. However, if we released test chips with trench structures in HF, we observed a much higher lateral etch rate for the oxide in the trench compared to the oxide elsewhere. To rule out any effects originating from the interface between the silicon and the oxide cladding we introduced a thin silicon dioxide layer (created with LTO) as interface layer. FIG. 24 shows the cleaved cross section of the test structure before (left) and after the HF etch (right). The red circle #1 points out that there is still LTO left in the corners of the trench, which shows that the lateral etch rate of the LTO is lower compared to the lateral etch rate of FOX in the trench. However, circle #2 shows that the lateral etch rates for both layers (LTO and FOX) are comparable outside the trench. This suggests that the high internal stress of the FOX layer in the trench has an influence on the lateral etch rate. Since no defects are visible in the optical microscope and scanning electron microscope, we assume that the stress creates nanometer size cracks along the trench which allow a significant increase of the etch rate in HF along the trench. FIG. 25 shows a top view of an etch SOI wafer with trench structure, LTO, FOX, and SiN. The difference in the etch rates is clearly visible. We can see an etch rate of 160 nm $min^{-1}$ on the planar surface and 4800 nm $min^{-1}$ in the trench.

Another indicator for nanometer size cracks along the trench was found in a second etch experiment with BOE. BOE is known to attack silicon dioxide, but due to a different surface tension it doesn't creep into narrow cracks. The second etch experiment shows a significantly smaller difference between the lateral etch rate in the trench and on planar surface.

Figure 6:
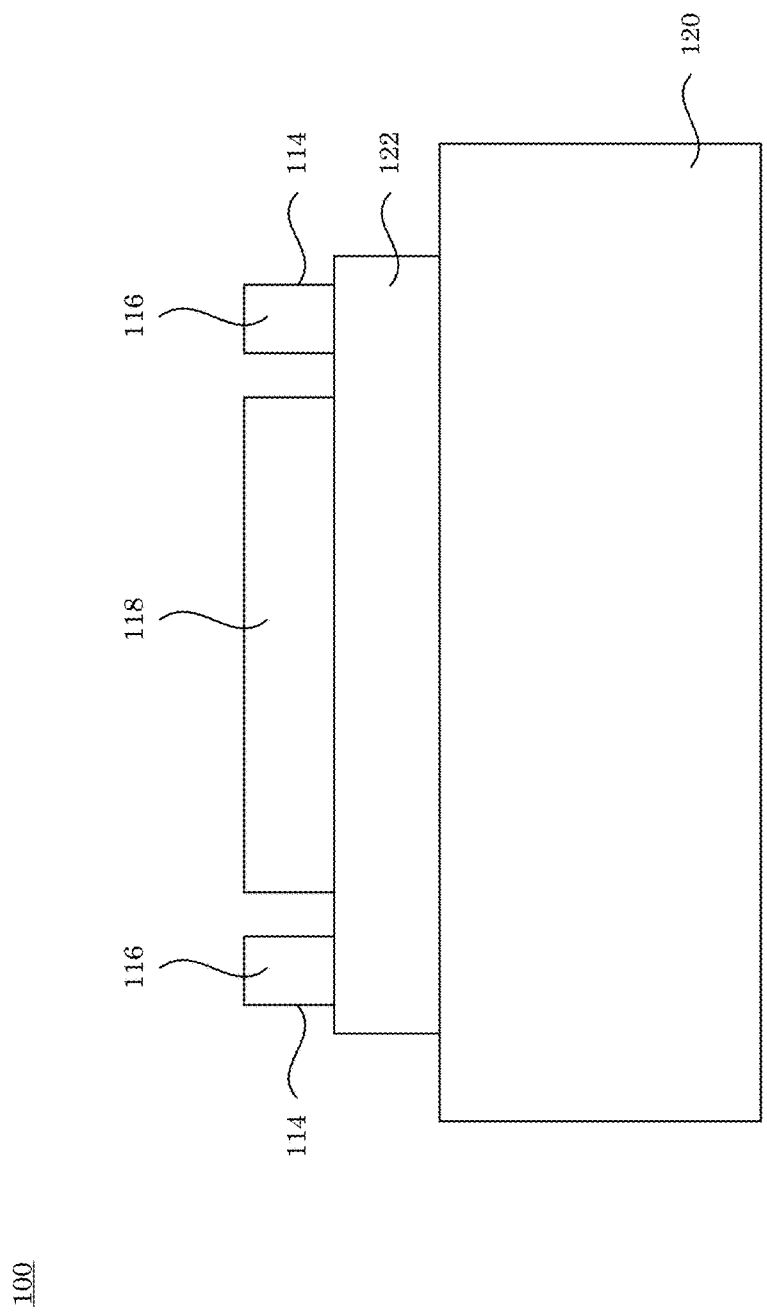
FIG. 6 shows a cross-section along line B-B of the microfabricated optical probe shown in FIG. 4.

The gap between the silicon micro disk and the mechanical member (i.e., cantilever or membrane) is important for the optical performance of the transducer. For smaller gaps, the optomechanical coupling increases exponentially. However, a smaller gap also decreases the optical quality factor of the disk due to increased loss of optical energy from the disk mode into the silicon nitride structure. Simulations show that a reasonable value for the gap is ≈400 nm. Therefore, to reach this value the cladding layer on top of the micro disk has to be thinned down to ≈400 nm. Furthermore, an anchor point is created to hold the photonic structures in place after the final removal of the silicon dioxide sacrificial layer. To improve the future anchor point of the micro disk and the transition, between the area with the thick LTO cladding and a thinner LTO layer on top of the disk, a combination of dry etching and wet oxide etching is used. The dry etch creates a step profile in the oxide and the wet etch is used to round the corners of this step profile as well as undercut the silicon micro disk around the future anchor point. FIG. 6 shows these process steps in detail.

A bottom antireflective coating (ARC) is used to decouple the optical properties of the sample from the lithography process. The correct thickness of this layer is essential for its functionality. A standard ARC used for this process is "AZ BARLi-II" with a final thickness of ≈180 nm. This is achieved with the spin coat parameter summarized below. The ARC is followed by a layer of positive photo resist ("SPR 220-3"). A resist thickness of ≈1.2 μm has been chosen, because it supplies enough resist for the etch processes as well as good coverage of all topographical steps. The process parameters are summarized in table 8.

TABLE 8

| Resist layer 1: BARLi II | |
|---|---|
| Spin speed: | ≈10.5 rad/s (≈100 rpm) for ≈5 s/≈209.4 rad/s f (≈2000 rpm) or ≈40 s |
| Soft bake: | ≈200° C. for ≈60 s |
| Resist layer 2: SPR 220-3 | |
| Spin speed: | ≈10.5 rad/s (≈100 rpm) for ≈5 s/≈314.2 rad/s (≈3000 rpm) for ≈40 s |
| Soft bake: | ≈115° C. for ≈90 s |

The wafer is exposed with 190 mJ/$cm^2$, a focus of 0.4 μm, a numerical aperture of 0.48, and a sigma of 0.5 in the "conventional" illumination mode. The resist is treated with a post exposure bake, of ≈110° C. for ≈60 s, to improve the result of the lithography process. In the following, the structure is developed in "AZ 300 MIF" for ≈60 s followed by a DIW rinse and dried with nitrogen.

Figure 26:
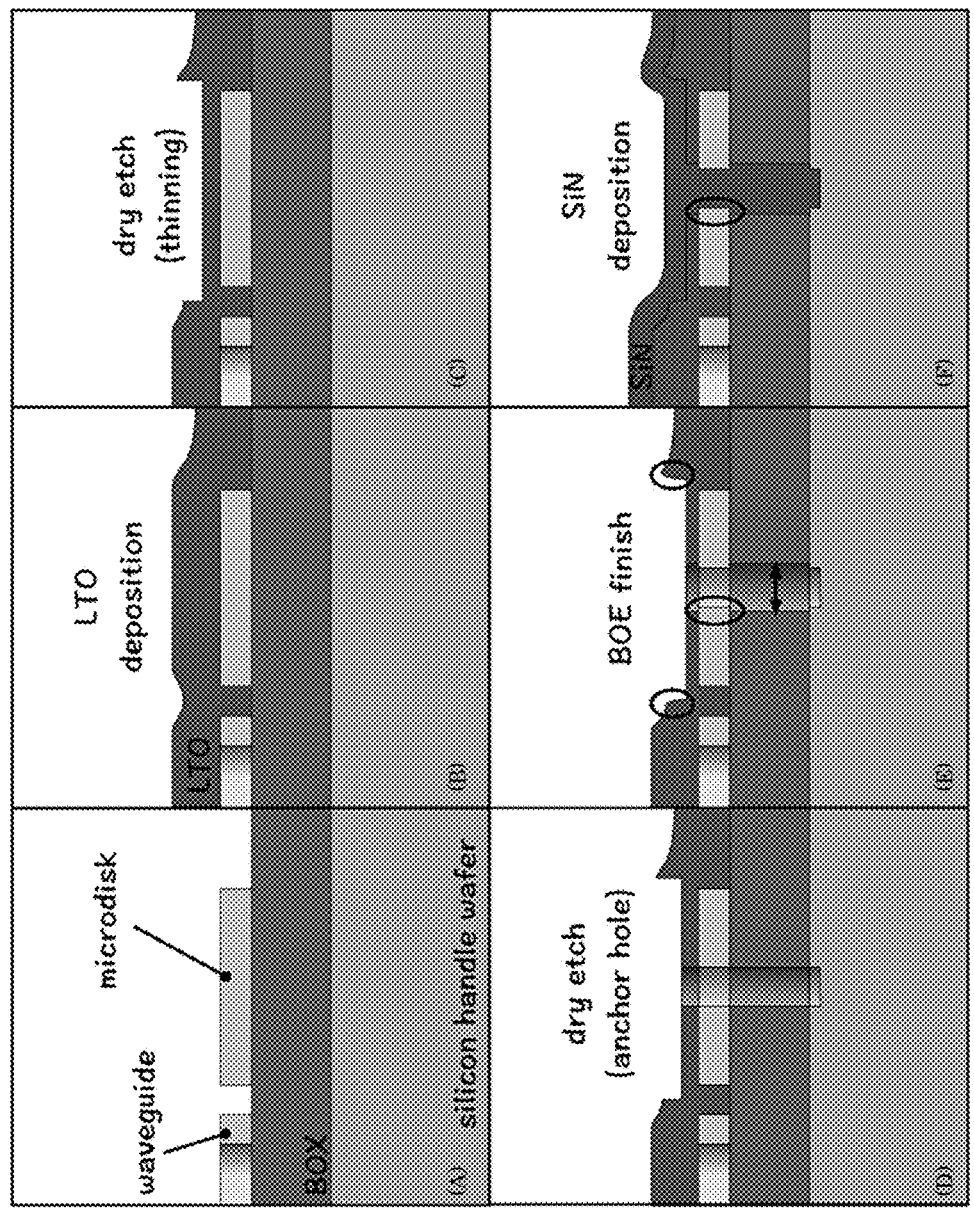
FIG. 26 shows process steps for: a) after the transfer of the photonic structure, b) formation of the cladding layer, c) dry etch step of the thinning process, d) dry etch of the anchor hole, e) BOE finishing of the coupling region and shaping of the anchor hole, and f) SiN deposition.

The transfer process starts with a long descum to remove the ARC at the bottom of the lithographically defined structures. The used oxygen plasma etch only removes the organic part of the ARC; the inorganic part will be removed in the following etch based on tetrafluoromethane chemistry. The etch step with tetrafluoromethane chemistry is also used to thin the oxide cladding layer in the region above the disk to a final thickness of ≈600 nm (FIG. 26c). The process parameters are summarized in the table 9, and the etch is performed in a parallel pate reactive ion etcher.

TABLE 9

| Descum | |
| --- | --- |
| Tool: | RIE |
| Time: | ≈7 min |
| Gases: | $O_2$/Ar |
| Flow rates: | ≈5 ml/min (≈5 sccm)/≈20 ml/min (≈20 sccm) |
| Pressure: | ≈4 Pa (≈30 mTorr) |
| RF power: | ≈50 W |
| Ref. RF power: | ≈0 W |
| $SiO_2$ | |
| Depth: | until a final cladding thickness of ≈600 nm above the silicon disk is reached |
| Gases: | $O_2$/$CF_4$ |
| Flow rates: | ≈5 ml/min (≈5 sccm)/≈25 ml/min (≈25 sccm) |
| Pressure: | ≈6.7 Pa (≈50 mTorr) |
| RF power: | ≈200 W |

The wafers are cleaned with a combination of solvents and acids to remove the plasma baked resist after the etching as well as the ARC. The first step of the cleaning is a solution based on N-Methyl-2-pyrrolidone (Resist remover 1165) at ≈70° C. for ≈15 min finished with a dump rinse. The next step is an acid clean with piranha solution ($H_2SO_4$:$H_2O_2$). The solution is used in a ratio of $H_2SO_4$:$H_2O_2$ (3:1) for ≈10 min, followed by a dump rinse. The last step is a solvent clean to remove the inorganic residuals of the ARC. The piranha solution can only remove the organic structure of the ARC but leaves the inorganic backbone of the resist on the surface. The recommended stripper for "AZ BARLi-II" is "AZ 300T stripper", which is used at ≈80° C. for ≈10 min, followed by a dry rinse and spin dry.

This lithography defines anchor holes, which go all the way down to the silicon handle wafer, to hold the released photonic structures in place. This requires a long etch process, which requires a UV cross linked resist to improve the resist performance during the etch. The first layer is an ARC which improves the adhesion between resist and sample. The ARC is followed by a layer of positive photo resist ("SPR 220-3"). A resist thickness of ≈3.1 μm has been chosen, because it supplies enough resist for the etch processes as well as good coverage of all topographical steps. The process parameters are as follows.

Resist layer 2: SPR-220 3
 Spin speed: ≈10.5 rad/s (≈100 rpm) for ≈5 s/≈157 rad/s (≈1500 rpm) for ≈40 s
 Soft bake: ≈115° C. for ≈90 s The wafer is exposed with 200 mJ/cm$^2$, a focus of 1 μm, a numerical aperture of 0.48, and a sigma of 0.5 in the "conventional" illumination mode. The resist is treated with a post exposure bake, of ≈110° C. for ≈60 s, to improve the result of the lithography process. In the following, the structure is developed in "AZ 300 MIF" for ≈60 s followed by a DIW rinse and dried with nitrogen. Subsequently the wafer is exposed with UV light (≈300 kJ/cm$^2$) at a temperature of ≈90° C. This crosslinks the resist and lowers the etch rate in dry etch significantly.

The transfer process starts with a descum to remove the ARC at the bottom of the lithographically defined structures. The used oxygen plasma etch does only remove the organic part of the ARC the inorganic part will be removed in the following etch based on fluoroform ($CHF_3$) chemistry.

The etch step with fluoroform chemistry is used to etch through the LTO cladding layer, the silicon device layer, the buried oxide layer, and a few nm into the silicon handle wafer (FIG. 26d). The process parameters are summarized in table 10, the etch is performed in a parallel pate reactive ion etcher.

TABLE 10

| Descum | |
| --- | --- |
| Tool: | RIE |
| Time: | ≈7 min |
| Gases: | $O_2$/Ar |
| Flow rates: | ≈5 ml/min (≈5 sccm)/≈20 ml/min (≈20 sccm) |
| Pressure: | ≈4 Pa (≈30 mTorr) |
| RF power: | ≈50 W |
| Ref. RF power: | ≈0 W |
| $SiO_2$ | |
| Depth: | until the silicon handle wafer is reached |
| Gases: | $O_2$/$CHF_3$ |
| Flow rates: | ≈5 ml/min (≈5 sccm)/≈45 ml/min (≈45 sccm) |
| Pressure: | ≈6.7 Pa (≈50 mTorr) |
| RF power: | ≈200 W |
| Ref. RF power: | ≈0 W |
| DC Bias: | ≈516 V |
| Etch rate: | ≈35 nm/min ($SiO_2$)/≈20 nm/min (Si) |

The wafers are cleaned with a combination of solvents and acids to remove the plasma baked resist after the etching as well as the ARC. Followed by an RCA clean and a BOE etch to complete the thinning process as well as the formation of the anchor holes. The first step of the cleaning is using a solution based on N-Methyl-2-pyrrolidone (Resist remover 1165) at ≈70° C. for ≈15 min finished with a dump rinse. The next step is an acid clean with piranha solution ($H_2SO_4$:$H_2O_2$). The solution is used in a ratio of $H_2SO_4$:$H_2O_2$ (3:1) for ≈10 min, followed by a dump rinse. The last step is a solvent clean to remove the inorganic residuals of the ARC. The recommended stripper for "AZ BARLi-II" is "AZ 300T stripper", which is used at ≈80° C. for ≈10 min, followed by a dry rinse and spin dry. Subsequently an RCA clean as described earlier (3.1.5) is performed. The RCA clean is followed by a wet oxide etch to complete the thinning process as well as the formation of the anchor holes. Diluted buffered hydrofluoric acid (BOE 6:1) is used for this etch, because this acid smooths the oxide step but does not attack the interfaces between silicon and silicon dioxide, as would be attacked by diluted hydrofluoric acid. The sample is exposed to the diluted BOE (6:1) for ≈1 min and 30 s to remove ≈200 nm of silicon dioxide (FIG. 26e), followed by a dump rinse and dry.

Low stress silicon nitride is used as the mechanical material because it has high etch resistivity against hydrofluoric acid and potassium hydroxide. The final thickness of the silicon nitride layer is ≈400 nm with the net tensile stress of ≈300 MPa (FIG. 26f). The deposition is performed at ≈850° C. The wafer boat is filled with dummy wafers and one clean bare silicon wafer on both sides of the SOI wafer to aid in uniformity.

As relates to electrodes and wire bond pads, the metal lines and wire bond pads, to connect the cantilever chip to a printed circuit board (PCB), are created in a metal lift off process. The process is based on "Lift-off" resist in combination with a positive photoresist. Chromium and Gold (Cr/Au) are used as metals. The Cr functions as an adhesion layer for the Au. This combination is not attacked by the HF and KOH, and is stable to temperatures of up to 350° C. A stack of three resist layers is used for the "Lift-off" process. The first layer is the ARC, followed by a layer of "Lift-off" resist, and finalized by a layer of positive photo resist. "Lift-off" resist is usually based on the solvent 1-methoxy-2-propanol to avoid mixing with the positive photoresist, which is usually based on anisole as solvent. "Lift-off" resist is not photo sensitive and therefore it is non-selectively dissolved by the developer, which creates an undercut of the photoresist layer. This undercut can be tuned with the soft bake temperature and time and is very important for a clean and reproducible "lift-off" process. After the lithography process, the sample has to be treated with an descum process and a short etch based on fluoroform chemistry, to remove the ARC at the bottom of the lithographically defined structures, to expose the silicon nitride below. The short dry etch also etches into the silicon nitride which further improves the adhesion of the metal to the silicon nitride.

The resist stack starts with an ARC prepared as previously described. The second layer consist out of the "Lift-off" resist ("LOR 3A") followed by a layer of positive photoresist. Parameters for the preparation of these three layers are listed in table 11.

TABLE 11

| Resist layer 1: Barli II | |
| --- | --- |
| Spin speed: | ≈10.5 rad/s (≈100 rpm) for ≈5 s/≈209.4 rad/s (≈2000 rpm) for ≈40 s |
| Soft bake: | ≈200° C. for ≈60 s |
| Typ. thickness: | ≈180 nm |
| Resist layer 2: LOR 3A | |
| Spin speed: | ≈10.5 rad/s (≈100 rpm) for ≈5 s/≈314 rad/s (≈3000 rpm) for ≈40 s |
| Soft bake: | ≈210° C. for ≈20 min |
| Typ. thickness: | ≈300 nm |
| Resist layer 3: SPR-220 3 | |
| Spin speed: | ≈10.5 rad/s (≈100 rpm) for ≈5 s/≈314 rad/s (≈3000 rpm) for ≈40 s |
| Soft bake: | ≈115° C. for ≈90 s |
| Typ. thickness: | ≈1200 nm |

The wafer is exposed with two different doses to clear the deep anchor hole and avoid overdosing the other structures. The first exposure is for all metal lines. This exposure uses 160 mJ/cm$^2$, a focus of 0.2 μm, a numerical aperture of 0.48, and a sigma of 0.5 in the "conventional" illumination mode. The second exposure is for all anchor holes and deep trenches. This exposure uses 200 mJ/cm$^2$, a focus of 0.6 μm, a numerical aperture of 0.48, and a sigma of 0.5 in the "conventional" illumination mode.

The resist is treated with a post exposure bake, of ≈110° C. for ≈60 s. In the following, the structure is developed in "AZ 300 MIF" for ≈60 s followed by a DIW rinse and nitrogen dry As relates to descum and removal of the ARC, the transfer process starts with a descum to remove the ARC at the bottom of the lithographically defined structures. The etch step with fluoroform chemistry is used to remove the residual of the ARC and to etch into the first few nanometers of the silicon nitride layer for an improvement of the adhesion between the metal and the silicon nitride layer. The process parameters are listed in table 12, and the etch is performed in a parallel plate reactive ion etcher.

TABLE 12

| Descum | |
| --- | --- |
| Tool: | RIE |
| Time: | ≈7 min |
| Gases: | O$_2$/Ar |
| Flow rates: | ≈5 ml/min (≈5 sccm)/≈20 ml/min (≈20 sccm) |
| Pressure: | ≈4 Pa (≈30 mTorr) |
| RF power: | ≈50 W |
| Ref. RF power: | ≈0 W |
| ARC + SiN | |
| Time: | ≈1 min |
| Gases: | O2/CHF3 |
| Flow rates: | ≈5 ml/min (≈5 sccm)/≈45 ml/min (≈45 sccm) |
| Pressure: | ≈6.7 Pa (≈50 mTorr) |
| RF power: | ≈200 W |
| Ref. RF power: | ≈0 W |
| DC Bias: | ≈516 V |
| Etch rate: | ≈35 nm/min |

The metal is deposited via evaporation. The adhesion of the metal layer is to the silicon nitride, wherein the descum is done shortly before the loading of the wafers. Furthermore, the Cr crucible is clean of any contamination. The Cr is deposited at a rate of 0.05 nm/s until a final thickness of 10 nm is reached. The Au is deposited at a rate of 0.25 nm/s until a final thickness of 120 nm is reached. "Lift-off" process is completed by dissolving the resist mask with a solvent solution based on N-Methyl-2-pyrrolidone at ≈70° C. for ≈3 h. The ARC is removed with piranha solution and "AZ 300T."

As relates to structuring of the mechanical member, the mechanical member of the transducer is shaped out of the silicon nitride layer. The shape is defined with a positive photoresist mask. Furthermore, the metal layer serves as a hard mask to improve the overlay error in critical regions. The lithography is based on ARC and positive photoresist. A dry etch process is used to transfer the structure into the silicon nitride layer. The etch chemistry based on fluoroform creates an etch rate of ≈60 nm/min for silicon nitride and ≈30 nm/min for the silicon dioxide layer underneath. The silicon nitride layer is over etched to ensure a good pattern transfer across all topographical steps.

The resist layers are prepared as described previously. The resist is exposed with 190 mJ/cm$^2$, a focus of 0.4 μm, a numerical aperture of 0.48, and a sigma of 0.5 in the "conventional" illumination mode. The resist is treated with a post exposure bake, of ≈110° C. for ≈60 s. In the following, the structure is developed in "AZ 300 MIF" for ≈60 s followed by a DIW rinse and nitrogen dry.

The pattern transfer starts with a descum step to remove the ARC at the bottom of the lithographically defined structures. The etch step with fluoroform chemistry is used to remove the residual of the ARC and to etch through the silicon nitride layer into the silicon dioxide layer. The process parameters are listed in table 13, and the etch is performed in a parallel pate reactive ion etcher.

TABLE 13

| Descum | |
| --- | --- |
| Tool: | RIE |
| Time: | ≈7 min |
| Gases: | O$_2$/Ar |
| Flow rates: | ≈5 ml/min (≈5 sccm)/≈20 ml/min (≈20 sccm) |

TABLE 13-continued

| | |
|---|---|
| Pressure: | ≈4 Pa (≈30 mTorr) |
| RF power: | ≈50 W |
| Ref. RF power: | ≈0 W |
| ARC + SiN + SiO$_2$ | |
| Time: | ≈1 min |
| Gases: | O2/CHF3 |
| Flow rates: | ≈5 ml/min (≈5 sccm)/≈45 ml/min (≈45 sccm) |
| Pressure: | ≈6.7 Pa (≈50 mTorr) |
| RF power: | ≈200 W |
| Ref. RF power: | ≈0 W |
| DC Bias: | ≈516 V |
| Etch rate: | ≈60 nm/min (SiN)/≈30 nm/min (SiO$_2$) |

The sample is cleaned with piranha solution followed by "AZ 300K."

As relates to hard mask preparation for anisotropic etch, in the following step, a hafnium oxide (HfO) hard mask is deposited on the wafer to protect the frontside, specifically the exposed areas of LTO, from potassium hydroxide (KOH), which is used to etch V-grooves into the frontside of the wafer and to shape the backside of the cantilever chip. The quality of the HfO layer is very important to ensure proper protection of the frontside. The etch rate of HfO in KOH depends on the carbon content of the HfO layer. The carbon content originates from the organic molecule (tetrakis(ethylmethylamino)hafnium (TEMAH)) which is used in the atomic layer deposition (ALD) process. The content of carbon in the final layer can be lowered by the use of a plasma induced deposition and with an increase purge time, as well as purge flow rates. The HfO layer is later patterned with the openings for the KOH etch on the front- and backside of the wafer. The used process for the lithography and pattern transfer is very similar for both sides. The lithography is performed in a frontside and backside contact mask aligner lithography. The pattern is transferred with a sulfur hexafluoride chemistry into the HfO layer and a fluoroform chemistry for the transfer into the underlying SiN/SiO$_2$/Si/SiO$_2$ until the silicon handle wafer is reached.

As relates to hafnium oxide deposition, the parameters chosen for the HfO deposition are listed in table 14. The parameters are separated into the seven steps of the ALD process (surface cleaning, deposition, TEMAH dose, TEMAH purge, gas stabilization, O$_2$ plasma, plasma purge). The final thickness of the ALD layer is ≈20 nm, which provides enough protection against KOH and can encapsulate small contaminations on the wafer surface.

TABLE 14

| Cleaning | |
|---|---|
| Recipe: | H2 surface clean |
| Pressure: | ≈7.5 × 10$^{-7}$ Pa |
| Gas: | H2 |
| Flow rate: | ≈15 ml/min (≈15 sccm) |
| Time (etch): | ≈5 min |
| Temperature: | ≈300° C. |
| Time (purge): | ≈1 min |
| Deposition | |
| Recipe: | opt_HfO |
| Cycles: | 200 |
| Pressure: | ≈7.5 × 10$^{-7}$ Pa |
| Temperature: | ≈300° C. |

TABLE 14-continued

| TEMAH dose | |
|---|---|
| Time: | ≈0.6 s |
| Gases: | Ar/TEMAH |
| Flow rate: | ≈250 ml/min (≈250 sccm)/≈1 mL/min (≈1 sccm) |
| TEMAH purge | |
| Time: ≈5 s | |
| Gases: Ar/O$_2$ | |
| Flow rate: ≈100 ml/min (≈100 sccm)/≈50 mL/min (≈50 sccm) | |
| Opt_gas stabil | |
| Time: ≈1 s | |
| Gases: O$_2$ | |
| Flow rate: ≈60 ml/min (≈60 sccm) | |
| O$_2$ plasma | |
| Time: ≈2 s | |
| Gases: O$_2$ | |
| Flow rate: ≈60 ml/min (≈60 sccm) | |

The wafer surface is prepared with hexamethyldiloxane. A thick positive photoresist is used to cover all topographical steps ("AZ 10xT"). The resist is applied with a spin coater with a spin speed of ≈10.47 rad/s (≈100 rpm) for ≈5 s followed by ≈418.88 rad/s (≈4000 rpm) for ≈45 s to create a final resist thickness of ≈10 μm. The resist is soft baked ≈110° C. for ≈180 s. The wafer is exposed in a mask aligner lithography with a dose of ≈1000 mJ/cm$^2$. The pattern is developed in diluted "AZ 400K" (1:3) for ≈180 s followed by a DIW rinse and dried with nitrogen The pattern transfer starts with a sulfur hexafluoride chemistry to transfer the structure into the HfO layer. This etch is followed by an etch based on fluoroform chemistry to transfer the structure into the underlying SiN/SiO$_2$/Si/SiO$_2$ $_{until}$ the silicon handle wafer is reached. The process parameters are listed in table 15, and the etch is performed in a parallel pate reactive ion etcher.

TABLE 15

| HfO | |
|---|---|
| Tool: | RIE |
| Time: | ≈5 min |
| Gases: | SF6/CF4 |
| Flow rates: | ≈6 ml/min (≈6 sccm)/≈24 mL/min (≈24 sccm) |
| Pressure: | ≈1 Pa (≈8 mTorr) |
| RF power: | ≈200 W |
| Ref. RF power: | ≈0 W |
| DC Bias: | ≈516 V |
| Etch rate: | ≈10 nm/min (HfO) |
| SiO$_2$/SiN/Si | |
| Tool: | RIE Unaxis 790 |
| Depth: | until the silicon handle wafer is exposed |
| Gases: | O2/ChF$_3$ |
| Flow rates: | ≈5 ml/min (≈5 sccm)/≈45 mL/min (≈45 sccm) |
| Pressure: | ≈6.7 Pa (≈50 mTorr) |
| RF power: | ≈200 W |
| Ref. RF power: | ≈0 W |
| DC Bias: | ≈516 V |
| Etch rate: | ≈35 nm/min |

As relates to backside lithography and pattern transfer, the process steps or previously described and or repeated on the backside of the wafer to define the openings for the backside anisotropic etching. The resist on the front side of the wafer is used as frontside protection during the backside lithography and pattern transfer process.

As relates to bulk micromachining, this step defines the frontside V-grooves for the fiber attachment and it shapes the cantilever chip to make it compatible with commercial scanning probe microscopes. The anisotropic etching process is separated into two parts. In the first part, the front- and backside are etched simultaneously until the V-grooves on the front side reach the final depth of ≈80 μm. At this point, the wafer is placed in an etch chuck to physically protect the frontside of the wafer from the etch solution and expose only the backside of the wafer. The backside is then etched until the backside etch reaches the frontside of the wafer and the membrane around the chip changes from a red, to an orange, and then to a clear color in the transmitted light. At this point, all the silicon on the membrane is gone and only the silicon dioxide membrane is left over.

The photoresist on the front- and backside of the wafer is removed with N-Methyl-2-pyrrolidone at ≈110° C. for ≈15 min followed by a dump rinse and spin dry.

The wafer is etched with a 30% solution of KOH in DIW at a temperature of ≈60° C. The beaker should be covered to avoid a change in concentration due to evaporation Both sides are etched until the final depth of ≈80 μm for the frontside V-grooves is reached. At this point, the wafer is placed in an etch chuck to physically protect the frontside of the wafer from the etch solution and expose only the backside of the wafer. The etch is continued at ≈80° C. for ≈16 h. Until the backside etch reaches the front side of the wafer and the membrane around the chip changes from a red, to an orange, and then to a clear color in the transmitted light. At this point, all the silicon on the membrane is gone and only the silicon dioxide membrane is left over. wafer can be removed from the chuck and cleaned in warm DIW several times followed by a clean in IPA and a careful drying with nitrogen.

As relates to release, the final release step consists out of a cleaning with HCl and DIW, followed by an HF sacrificial layer etch, which is completed with an intensive rinse with DIW. After the DIW rinse, the wafer is placed into several batches of IPA to replace the DIW in all cavities with IPA. The wafer should stay in every bath for a couple of minutes. After all the DIW is replaced with IPA, the wafer is placed in a critical point dryer to critical point dry the released transducer.

As relates critical point drying, the release starts with a cleaning in HCl for ≈10 min to remove residuals of KOH followed by a dump rinse cycle until a sufficient bath resistivity is reached again. After the wafer is cleaned, the HfO protection layer and $sio_2$ sacrificial layer are etched in HF (49%) until all mechanical structures are sufficiently undercut. The release etch for the described structure is ≈4 min and 30 s, which results in an undercut of ≈7 μm. The HF etch is followed by extensive dump rinse cycles to remove all HF residuals form the substrate. In the following is the DIW replaced with IPA. This takes place in several bathes, each bath ≈10 min before the sample is placed in the critical point dryer to dry the released transducers.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A microfabricated optical probe comprising:
    a cantilever;
    an optical waveguide disposed at a periphery of the cantilever and comprising an optical loop, the optical loop being disposed proximal to the cantilever free end; and
    a substrate on which the cantilever is disposed and from which the cantilever and the optical loop protrude,
    wherein the waveguide is mechanically connected to the cantilever such that the cantilever and waveguide move together
    wherein the cantilever and the optical waveguide flex independently of the substrate.

2. The microfabricated optical probe of claim 1, further comprising:
    a first optical cladding layer interposed between the waveguide and the substrate,
    wherein the optical loop protrudes from the first optical cladding layer.

3. The microfabricated optical probe of claim 2, further comprising:

a cover layer disposed on the waveguide such that the waveguide is interposed between the substrate and the cover layer.

4. The microfabricated optical probe of claim 3, the cover layer extends beyond the substrate, comprises the cantilever, and exposes the optical loop of the optical waveguide.

5. The microfabricated optical probe of claim 3, further comprising:
a second optical cladding layer interposed between the waveguide and the cover layer,
wherein the optical loop protrudes from the second optical cladding layer.

6. The microfabricated optical probe of claim 1, wherein the optical waveguide receives primary light and communicates some of the primary light into a photonic device disposed proximate to the optical loop as a result of evanescent coupling between the optical loop and the photonic device.

7. The microfabricated optical probe of claim 1, wherein the optical waveguide receives secondary light from a photonic device disposed proximate to the optical loop as a result of evanescent coupling between the optical loop and the photonic device, and communicates some of the secondary light as output.

8. The microfabricated optical probe of claim 6, wherein the cantilever mechanically deforms in response to mechanical contact between the optical loop and a photonic device.

9. The microfabricated optical probe of claim 8, further comprising:
a first single mode optical fiber in optical communication with the optical waveguide and that communicates primary light to the optical waveguide.

10. The microfabricated optical probe of claim 9, further comprising:
a second single mode optical fiber in optical communication with the optical waveguide and that receives output light from the optical waveguide.

11. The microfabricated optical probe of claim 10, wherein the optical waveguide further comprising:
a first arm in optical communication with the first single mode optical fiber to receives the primary light from the first single mode optical fiber.

12. The microfabricated optical probe of claim 11, wherein the optical waveguide further comprising:
a second arm in optical communication with the second single mode optical fiber to communicate the output light to the second single mode optical fiber.

* * * * *